(12) United States Patent
Bandyopadhyay et al.

(10) Patent No.: US 9,290,473 B2
(45) Date of Patent: Mar. 22, 2016

(54) INHIBITORS OF PHOSPHATIDYLINOSITOL-3-KINASE (PI3) AND INDUCERS OF NITRIC OXIDE (NO)

(75) Inventors: Santu Bandyopadhyay, Kolkata (IN); Bikas Chandra Pal, Kolkata (IN); Jaisankar Parasuraman, Kolkata (IN); Siddhartha Roy, Kolkata (IN); Jayashree Bagchi Chakrabotry, Kolkata (IN); Indrani Choudhury Mukherjee, Kolkata (IN); Sanjit Kumar Mahato, Kolkata (IN); Aditya Konar, Kolkata (IN); Srabanti Rakshit, Kolkata (IN); Labanya Mandal, Kolkata (IN); Dipyaman Ganguly, Kolkata (IN); Kausik Paul, Kolkata (IN); Anirban Manna, Kolkata (IN); Jayaraman Vinayagam, Kolkata (IN); Churala Pal, Kolkata (IN)

(73) Assignee: COUCIL OF SCIENTIFIC & INDUSTRIAL RESEARCH, New Delhi (IN)

(*) Notice: Subject to any disclaimer, the term of this patent is extended or adjusted under 35 U.S.C. 154(b) by 137 days.

(21) Appl. No.: 13/144,263

(22) PCT Filed: Jan. 12, 2010

(86) PCT No.: PCT/IB2010/000040
§ 371 (c)(1),
(2), (4) Date: Mar. 30, 2012

(87) PCT Pub. No.: WO2010/079423
PCT Pub. Date: Jul. 15, 2010

(65) Prior Publication Data
US 2012/0190738 A1    Jul. 26, 2012

(30) Foreign Application Priority Data
Jan. 12, 2009   (IN) .............................. 44/DEL/2009

(51) Int. Cl.
*A61K 31/36* (2006.01)
*C07C 215/54* (2006.01)
(Continued)

(52) U.S. Cl.
CPC ............ *C07D 317/06* (2013.01); *C07C 251/40* (2013.01); *C07C 251/66* (2013.01); *C07C 255/36* (2013.01); *C07C 255/38* (2013.01)

(58) Field of Classification Search
CPC .. C07C 251/40; C07C 251/66; C07C 255/36; C07C 255/38; C07D 317/06
See application file for complete search history.

(56) References Cited

U.S. PATENT DOCUMENTS

| | | |
|---|---|---|
| 4,838,924 A | 6/1989 | Takematsu |
| 5,948,909 A | 9/1999 | Buizer et al. |
| 7,091,238 B1 | 8/2006 | Sudo |

FOREIGN PATENT DOCUMENTS

| | | |
|---|---|---|
| DE | 27 01 586 | 7/1978 |
| EP | 0 261 977 A2 | 3/1998 |

(Continued)

OTHER PUBLICATIONS

Evans et al. (J. Agric. Food Chem., vol. 32, No. 6, 1984, pp. 1254-1256.*

(Continued)

*Primary Examiner* — Savitha Rao
(74) *Attorney, Agent, or Firm* — John P. White; Cooper & Dunham LLP

(57) ABSTRACT

The present invention relates to compounds of general formula 1 for the treatment of malignancy by inhibition of PI3-Akt pathway and or induction of NO. The present invention also relates to the use of compound of general formula 1 for the treatment of malignancy by inhibition of PI3-Akt pathway and or induction of NO. The present invention further relates to a method of treating malignancy by inhibition of PI3-Akt pathway and or induction of NO by administration of compound or said composition to a mammal in need thereof.

10 Claims, 9 Drawing Sheets

(51) Int. Cl.
  *C07C 255/33* (2006.01)
  *C07C 39/10* (2006.01)
  *C07D 317/06* (2006.01)
  *C07C 251/40* (2006.01)
  *C07C 251/66* (2006.01)
  *C07C 255/36* (2006.01)
  *C07C 255/38* (2006.01)

(56) References Cited

FOREIGN PATENT DOCUMENTS

EP          1 405 851 A1   4/2004
WO        WO 00/40575 A1   7/2000

OTHER PUBLICATIONS

Remington, the science and practice of pharmacy (19th edition, 1995) pp. 1682-1685 and pp. 1448-1523.*
DE 10010512 or Wo2001066097 Herrmann et al. abstract.*
International Search Report, mailed May 25, 2010 in connection with PCT International Application No. PCT/IB2010/000040, filed Jan. 12, 2010.
International Preliminary Report on Patentability (Chapter II of the Patent Cooperation Treaty), issued Mar. 13, 2011 in connection with PCT International Application No. PCT/IB2010/000040, filed Jan. 12, 2010.
Written Opinion of the International Searching Authority, issued Jul. 12, 2011 in connection with PCT International Application No. PCT/IB2010/000040, filed Jan. 12, 2010.
Chang et al. (2002) "Inducing the Cell Cycle Arrest and Apoptosis of Oral KB Carcinoma Cells by Hydroxychavicol: Roles of Glutathione and Reactive Oxygen Species" British Journal of Pharmacology, 135(3), 619-630.
Schöpf et al. (1940) "Die Synthese de 3-Oxy-4- methoxy-phenlacetaldehyds (Homoisovanillins) und des 3,4-Dioxyphenlacetaldehyds (Homoprotecatechualdehyds)" Justus Liebigs Annalen Der Chemie, 544(1), 30-62.
Gorda et al. (1988) "Studies on the Synthesis of Heterocyclic Compounds. XVI. Cleavage of 1,3- benzodioxoles and—benzoxathioles by Sodium Iodide-Acyl Chloride" Journal of Heterocyclic Chemistry, 25(1), 311-314.
"Safrole, Isosafrole, and Dihydrosaffrole" (1998) International Agency for Research on Cancer (IARC)—Summaries & Evaluations.
Verheijen et al. (2007) "Phosphatidylinositol 3- kinase (P13K) Inhibitors as Anticancer Drugs" Drugs of the Future, 32(6), 537-547.
Kohno et al. (2008) "A New Synthesis of the benzo[c]phenanthridines nornitidine, noravicine, and isodecarine, based on a microwave-assited electrocyclic reaction of the aza 6π-electron system" Tetrahedron Letters, 50(5), 590-592.
Hurd et al. (1930) "The Behavior of Allyl Derivatives of Catechol and Resorcinol Toward Heat" Journal of the American Chemical Society, 52(4), 1700-1706.
Zbiral et al. (1961) Thermische Umlagerung von Acetoxy-cyclohexadienonen, 2. Chemical Monthly, 92(3), 654-666.
Database Beilstein [Online] Beilstein Institute for Organic Chemsitry (1966) Database accession No. BRN: 2591937 (1966).
Database Beilstein [Online] Beilstein Institute for Organic Chemsitry (1966) Database accession No. BRN: 2578011 (1966).

* cited by examiner

2A

2B

2C

Scheme 1

Scheme 2

Scheme 3

INHIBITORS OF PHOSPHATIDYLINOSITOL-3-KINASE (PI3) AND INDUCERS OF NITRIC OXIDE (NO)

CROSS-REFERENCE TO RELATED APPLICATIONS

This application is a §371 national stage of PCT International Application No. PCT/IB2010/000040, filed Jan. 12, 2010, claiming priority of Indian Application No. 44/DEL/2009, filed Jan. 12, 2009, the contents of each of which are hereby incorporated by reference into this application.

FIELD OF THE INVENTION

The present invention relates to compounds of general formula 1 for the treatment of malignancies(cancers). Malignancies may be treated by the inhibition of phosphatidylinositol-3-kinase (PI3) pathway or by inducing nitric oxide (NO).

BACKGROUND OF THE INVENTION

Cancer or malignancy is the result of uncontrolled growth of a given cell type that occurs together with invasion of the surrounding tissue and the spread of malignant cells. Molecular evidence suggests the important roles for PI3 signaling pathway in tumor promotion and progression (Nature Rev. Drug Discovery 2005, 4, 988-1003).

References may be made to Journal "Nature Rev. Drug Discovery 2005, 4, 988-1003PI3" wherein signaling pathway abnormalities are common in many cancers regardless of their origin, for example breast, prostate, pancreas, acute lymphoblastic leukemia, chronic myelogenous leukemia. Therefore, inhibition of PI3 signaling pathway by molecules is an efficient approach for the development of novel drugs for treating diseases such as cancers of different origin.

PI3 inhibitors have anticancer properties. For example, Wortmannin and LY 294002 have antitumor activity in vitro and in vivo, and sensitize tumor cells to other targeted therapeutics, chemotherapy and radiation (Clin. Cancer Res. 1997, 3, 1149-1156; Clin. Cancer Res. 2001, 7, 3269-3275; Leuk. Res. 2000, 24, 917-925; Cancer Res. 2002, 62, 1087-1092).

High levels of intracellular nitric oxide (NO) production cause S-nitrosylation of a number of proteins leading to cell death (Nature Cell Biology 2005, 7, 645-646).

Hydroxychavicol is known to induce cell cycle arrest and apoptosis in oral KB carcinoma cell line (Cell. Mol. Life Sci., 2004, 61, 83-96) and in hepatocarcinoma cells (Cancer lett., 2000, 155, 29-35). Hydroxychavicol has anti-oxidative property inducing cell-cycle arrest and apoptosis of oral KB carcinoma cells (British Journal of Pharmacology, 2002, 135, 619-630), anti-mutagenic property against tobacco-specific carcinogens (Mutat. Res., 1989, 210,249-253), as well as chemopreventive activity against benzo[a]pyrene induced forestomach tumors in mice (J. Ethnopharmacol., 1991, 34, 207-213). Conflicting literature exists on the effect of hydroxychavicol on cycloxygenase 2: while one report suggested enhancement of expression (J. Oral Pathol. Med., 2003, 32, 522-529), another report suggested hydroxychavicol-mediated inhibition of platelet aggregation by suppression of cyclooxygenase, thromboxane production and calcium mobilization (British Journal of Pharmacology, 2007, 152, 73-82). Hydroxychavicol is a potent COX-1/COX-2 inhibitor and could be potentially used in prevention or treatment of cardiovascular disease through its anti-inflammatory effect (British Journal of Pharmacology, 2007, 152, 73-82). The chemopreventive efficacy of betel leaf extract and its constituents, including hydroxychavicol on 7,12-dimethylbenz(a)anthracene induced skin tumors in mouse, has been reported (Indian Journal of Experimental Biology, 1991, 29, 346-351). The anti-mutagenic and anti-carcinogenic properties of hydroxychavicol and eugenol have been reported (Mutagenesis, 1989, 4, 200-204). Another recent report suggested that allylpyrocatechol (hydroxychavicol) inhibitied NF-κB pathway in lipopolysaccharide (LPS)-induced macrophages leading to suppression of iNOS, interleukin-12 and TNF-α (International Immunopharmacoloty, 2008, 8, 1264-1271).

The present invention relates to inhibition of prosurvival pathway PI3-Akt. The phosphatidylinositol-3-kinase (PI3)/AKT signaling pathway is crucial to many aspects of cell growth and survival. The PI3/Akt pathway is activated in cancer (Nature Reviews Drug Discovery, 2005, 4, 988-1003) making this pathway an optimal target for cancer therapy. The present invention also relates to production of NO (nitric oxide) by hydroxychavicol in cancer cells. Experiments with siRNAs identified endothelial nitric oxide synthase (eNOS) as the producer of hydroxychavicol mediated NO.

Hydroxychavicol has some inherent problem of arial autooxidation leading to production of super oxide and hydrogen peroxide (Mutation Research, 2004, 565, 35-44). Autooxidation makes this molecule very unstable. We therefore prepared some derivatives of hydroxychavicol which lack autooxidation potential making the molecules more stable. At the present time, the inventors are not aware of any prior arts that discloses that hydroxychavicol or its derivates inhibit PI3 signaling pathway and or induce nitric oxide in cancer cells.

OBJECTIVE OF THE INVENTION

The main objective of the present invention is to provide compounds of general formula 1 for the treatment of malignancies (cancer).

Another objective of the present invention is to provide compounds of general formula 1 for the treatment of malignancies (cancer) of breast, prostate, pancreas, acute lymphoblastic leukemia, and acute/chronic myelogenous leukemia.

Another objective of the present invention is that the malignancies may be treated by PI3 (phosphatidylinositol-3-kinase) pathway inhibition or by nitric oxide production.

Another objective of the present invention is to provides a method of inhibition of PI3 pathway or induction of Nitric oxide (NO) by administering the compound of general formula 1 containing such a compound to a mammal in need thereof.

SUMMARY OF THE INVENTION

Accordingly, present invention provides compounds of general formula

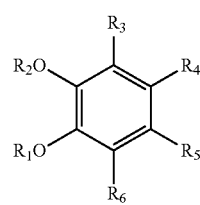

General formula 1 wherein
R$_1$=H or COCH$_3$
R$_2$=H or COCH$_3$
R$_1$+R$_2$=—CH$_2$—
R$_3$=H or CH$_2$—CH=CH$_2$
R$_4$=H or CH$_2$—CH=CH$_2$ or CH$_2$—CH$_2$—CH$_3$ or C(CH$_3$)$_2$CH=NOH or
C(CH$_3$)$_2$CH=CH$_2$ or C(CH$_3$)$_2$CN or C(CH$_3$)$_2$CH=NOCOCH$_3$
R$_5$=H or CH$_2$—CH=CH$_2$
R$_6$=H or CH$_2$—CH=CH$_2$ In an embodiment of the invention, represented compounds comprising:
3,4-diallyl-1,2-phenylene diacetate;(6)
2-(3,4-dihydroxyphenyl)-2-methylpropanal oxime;(9)
2-(3,4-dihydroxyphenyl)-2-methylpropanenitrile;(10)
4-(2-cyanopropan-2-yl)-1,2-phenylene diacetate;(11)
4-(1-(acetoxyimino)-2-methylpropan-2-yl)-1,2-phenylene diacetate;(12)
5-(2-methylbut-3-en-2-yl)benzo[d][1,3]dioxole;(14)
3-allyl-4-propylbenzene-1,2-diol;(17)
3,4-diallyl-5-propylbenzene-1,2-diol;(18)
3-allyl-1,2-phenylene diacetate;(19)
3-allyl-4-propyl-1,2-phenylene diacetate; (20)and
3,4-diallyl-5-propyl-1,2-phenylene diacetate.(21)

In another embodiment of the invention, the structural formulae of the representative compounds are:

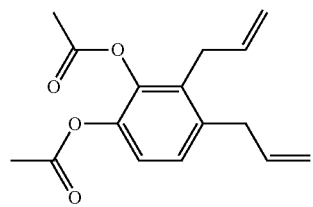

Compound 6

3,4-diallyl-1,2-phenylene diacetate

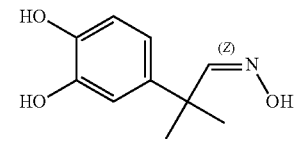

Compound 9

2-(3,4-dihydroxyphenyl)-2-methylpropanal oxime

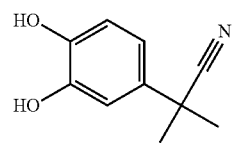

Compound 10

2-(3,4-dihydroxyphenyl)-2-methylpropanenitrile

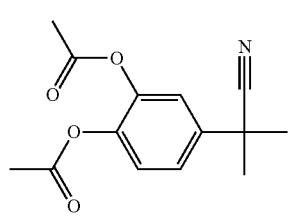

Compound 11

4-(2-cyanopropan-2-yl)-1,2-phenylene diacetate

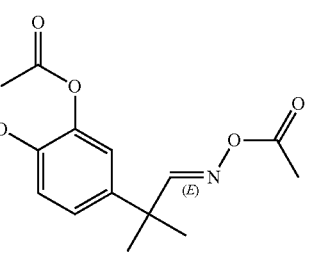

Compound 12

4-(1-(acetoxyimino)-2-methylpropan-2-yl)-1,2-phenylene diacetate

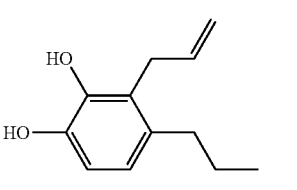

Compound 14

5-(2-methylbut-3-en-2-yl)benzo[d][1,3]dioxole

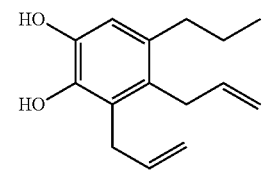

Compound 17

3-allyl-4-propylbenzene-1,2-diol

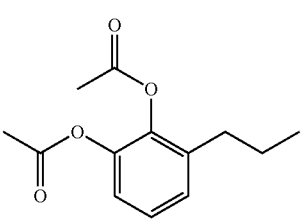

Compound 18

3,4-diallyl-5-propylbenzene-1,2-diol

Compound 19

3-ally-1,2-phenylene diacetate

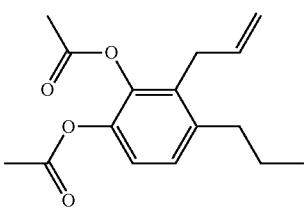

Compound 20

3-allyl-4-propyl-1,2-phenylene diacetate

-continued

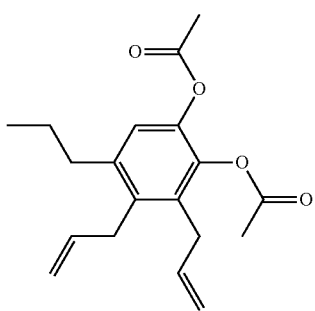

Compound 21

3,4-diallyl-5-propyl-1,2-phenylene diacetate

In yet another embodiment of the invention, the compounds are useful for the treatment of malignancy.

In yet another embodiment of the invention, the malignancy is characterized by phosphatidylinositol-3-kinase (PI3)/Akt pathway inhibition or by Nitric oxide induction.

In yet another embodiment of the invention, the malignancy is a malignancy of breast, prostate, pancreas, acute lymphoblastic leukemia, acute myelogenous leukemia, or chronic myelogenous leukemia.

In yet another embodiment of the invention, the compound is administered through oral, intravenous, intramuscular or subcutaneous route, to a mammal in need thereof.

In yet another embodiment of the invention, the compound is administered in a daily dose of 30 mg/kg of active ingredient to body weight to about 300 mg/kg of active ingredient to body weight, to a mammal in need thereof.

In yet another embodiment of the invention, pharmaceutical composition comprising compounds of general formula 1, 0.1 to 99% of compounds preferably 30 to 95% are used for tablets and capsules and 3-50% are used for liquid preparation are used along additives for the treatment of malignancy.

In yet another embodiment of the invention, additives are selected from the group consisting of fillers, antioxidants, dispersants, emulsifiers, flavors, preservatives, solubilizers and colorants.

In yet another embodiment of the invention, exhibiting in vitro activity against human cancer cell lines selected from the group consisting of Leukemia cancer cell lines (K562, KU812), acute myeloid leukemia cancer cell line (HL60, U937), T-lymphoblastic leukemia cell line (Molt-4), prostate cancer cell line (PC-3), breast cancer cell line (MCF-7) and pancreatic cancer cell line (MIA PaCa-2).

In yet another embodiment of the invention, concentration of the compounds 9, 10, 12, 14 and 19 of general formula 1 used for in vitro activity against chronic myeloid leukemia cancer cell lines (K562, KU812) for $IC_{50}$ is in the range of 13 to 657 µM.

In yet another embodiment of the invention, concentration of the compounds 9, 10, 12, 14 and 19 of general formula 1 used for in vitro activity against acute myeloid leukemia cancer cell line (HL60, U937) for $IC_{50}$ is in the range of 15 to 670 µM.

In yet another embodiment of the invention, concentration of the compounds 9, 10, 12, 14 and 19 of general formula 1 used for in vitro activity against T-lymphoblastic leukemia cell line (Molt-4) for $IC_{50}$ is in the range of 20 to 650 µM.

In yet another embodiment of the invention, concentration of the compounds 9, 10, 12, 14 and 19 of general formula 1 used for in vitro activity against prostate cancer cell line (PC-3) for $IC_{50}$ is in the range of 20 to 670 µM.

In yet another embodiment of the invention, concentration of the compounds 9, 10, 12, 14 and 19 of general formula 1 used for in vitro activity against breast cancer cell line (MCF-7) for $IC_{50}$ is in the range of 20 to 680 µM.

In yet another embodiment of the invention, concentration of the compounds 9, 10, 12, 14 and 19 of general formula 1 used for in vitro activity against pancreatic cancer cell line (MIA PaCa-2) for $IC_{50}$ is in the range of 20 to 680 µM.

In yet another embodiment of the invention, compounds of general formula 1, used for the treatment of malignancy wherein $R_1$=H or $COCH_3$
$R_2$=H or $COCH_3$
$R_3$=H or $CH_2$—CH=$CH_2$
$R_4$=H or $CH_2$—CH=$CH_2$ or $CH_2$—$CH_2$—$CH_3$ or $C(CH_3)_2CH$=$CHCOOC_2H_5$
$R_5$=H or $CH_2$—CH=$CH_2$
$R_6$=H In yet another embodiment of the invention, use of compounds of general formula 1 for the treatment of malignancy represented by:
4-allyl-benzene-1,2-diol (hydroxychavicol)(1);
4,5-diallylbenzene-1,2-diol (2);
3,4-diallylbenzene-1,2-diol(3);
4-allyl-5-propylbenzene-1,2-diol(4);
4,5-diallyl-1,2-phenylene diacetate(5);
4-allyl-1,2-phenylene diacetate(7);
4-allyl-5-propyl-1,2-phenylene diacetate(8);
(E)-ethyl 4-(3,4-dihydroxyphenyl)-4-methylpent-2-enoate(13);
(E)-4-(5-ethoxy-2-methyl-5-oxopent-3-en-2-yl)-1,2-phenylene diacetate(15);
3-allyl-benzene-1,2-diol (16).

In yet another embodiment of the invention, the malignancy is characterized by PI3 (phosphatidylinositol-3-kinase)/Akt pathway inhibition or by Nitric oxide induction.

In yet another embodiment of the invention, the malignancy is a malignancy of breast, prostate, pancreas, acute lymphoblastic leukemia, acute myelogenous leukemia, or chronic myelogenous leukemia.

In yet another embodiment of the invention, the compound is administered through oral, intravenous, intramuscular or subcutaneous route, to a mammal in need thereof.

In yet another embodiment of the invention, compounds exhibiting in vitro activity against human cancer cell lines selected from the group consisting of Leukemia cancer cell lines (K562, KU812), acute myeloid leukemia cancer cell line (HL60, U937), T-lymphoblastic leukemia cell line (Molt-4), prostate cancer cell line (PC-3), breast cancer cell line (MCF-7) and pancreatic cancer cell line (MIA PaCa-2).

In yet another embodiment of the invention, concentration of the compounds 1,2,3,7,13 and 16 used for in vitro activity against chronic myeloid leukemia cancer cell lines (K562, KU812) for $IC_{50}$ is in the range of 13 to 52 µM.

In yet another embodiment of the invention, concentration of the compounds 1,2,3,7,13 and 16 used for in vitro activity against acute myeloid leukemia cancer cell line (HL60, U937) for $IC_{50}$ is in the range of 13 to 60 µM.

In yet another embodiment of the invention, concentration of the compounds 1,2,3,7,13 and 16 used for in vitro activity against T-lymphoblastic leukemia cell line (Molt-4) for $IC_{50}$ is in the range of 15 to 50 µM.

In yet another embodiment of the invention, concentration of the compounds 1,2,3,7,13 and 16 used for in vitro activity againstprostate cancer cell line (PC-3)for $IC_{50}$ is in the range of 25 to 70 µM.

In yet another embodiment of the invention, concentration of the compounds 1,2,3,7,13 and 16 used for in vitro activity against breast cancer cell line (MCF-7) for $IC_{50}$ is in the range of 25 to 70 µM.

In yet another embodiment of the invention, concentration of the compounds 1,2,3,7,13 and 16 used for in vitro activity against pancreatic cancer cell line (MIA PaCa-2) for $IC_{50}$ is in the range of 30 to 70 µM.

In yet another embodiment of the invention, the compound is administered in a daily dose of 30 mg/kg of active ingredient to body weight to about 300 mg/kg of active ingredient to body weight, to a mammal in need thereof.

In yet another embodiment of the invention, Pharmaceutical composition comprising compounds wherein 0.1 to 99% of compounds preferably 30 to 95% are used for tablets and capsules and 3-50% are used for liquid preparation are used with additives for the treatment of malignancy.

In yet another embodiment of the invention, additives are selected from the group consisting of fillers, antioxidants, dispersants, emulsifiers, flavors, preservatives, solubilizers and colorants.

DETAILED DESCRIPTION OF THE INVENTION

Figure 1:
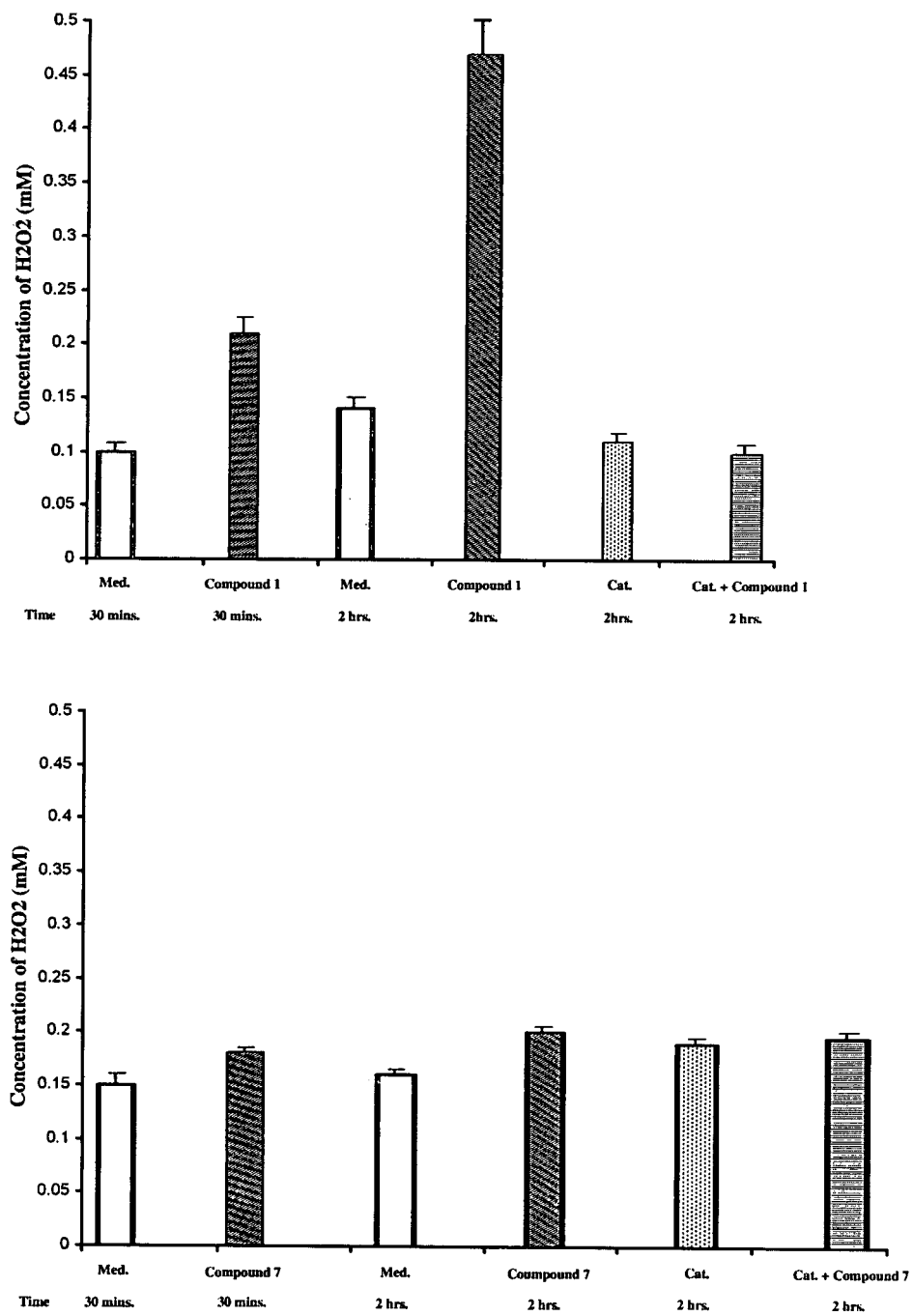
FIG. 1 shows compound 1 (hydroxychavicol) is sensitive to autooxidation but compound 7 is resistant to autooxidation.

The present invention provides a pharmaceutical composition including a compound of general formula 1 for the treatment of malignancies.

Compound 1 (hydroxychavicol) was obtained from Piper betle extract as described in Example 2. Compound 1 (hydroxychavicol) can also be prepared synthetically and this is described in Example 3. Synthesis of many of the compounds of general formula 1 was accomplished starting with commercially available catechol. The synthesis is shown in Schemes 1 and 2. The compounds of the present invention include the corresponding salts, isomers and polymorphs of the compounds of general formula 1.

The salts are pharmaceutically acceptable salts and are in particular salts which are non-toxic, or which can be used physiologically.

The term pharmaceutically acceptable salts is meant to include salts of the active compounds which are prepared with acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, oxalic, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like. Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

Certain compounds of the present invention can exist in unsolvated forms as well as solvated forms, including hydrated forms. In general, the solvated forms are equivalent to unsolvated forms and are intended to be encompassed within the scope of the present invention.

Certain, compounds of the present invention may exist in multiple crystalline or amorphous forms. In general, all physical forms are equivalent for the uses contemplated by the present invention and are intended to be within the scope of the present invention.

In addition to salt forms, the present invention provides compounds, which are in a prodrug form. Prodrugs of the compounds described herein are those compounds that readily undergo chemical changes under physiological conditions to provide the compounds of the present invention.

Additionally, prodrugs can be converted to the compounds of the present invention by chemical or biochemical methods in an ex vivo environment.

Various polymorphs of compounds of the present invention can be prepared by crystallization of the compounds under different conditions. The different conditions are, for example, using different commonly used solvents or their mixtures for crystallization; crystallization at different temperatures; various modes of cooling, ranging from very fast to very slow cooling during crystallizations. Polymorphs can also be obtained by heating or melting the compound followed by gradual or fast cooling. The presence of polymorphs can be determined by IR (Infra-red) spectroscopy, solid probe NMR (Nuclear Magnetic Resonance) spectroscopy, differential scanning calorimetry, powder X-ray diffraction or such other techniques.

The present invention includes all possible geometric or cis-trans (E/Z) isomers of the compounds of the present invention. In the case of a cis/trans isomerism the invention includes the Cis form and the Trans form as well as mixtures of these forms in all ratios. The preparation of individual isomers can be carried out, if desired, by separation of a mixture by customary methods.

The term "active ingredient" as used herein includes the compound of general formula 1.

The term "composition" includes formulations or other preparations that are suitable for administration to a mammal.

The term "treating", "treat" or "treatment" as used herein includes preventive (prophylactic) and palliative treatment.

As used herein, "safe and effective amount" means an amount of compound or composition, sufficient to significantly induce a positive modification in the condition to be regulated or treated, but low enough to avoid serious side effects (at a reasonable benefit/risk ratio), within the scope of sound medical judgment. The safe and effective amount of the compound or composition will vary with the particular condition being treated, the age and physical condition of the end user, the severity of the condition being treated/prevented, the duration of the treatment, the nature of concurrent therapy, the specific compound or composition employed, the particular pharmaceutically acceptable carrier utilized, and like factors. As used herein, all percentages are by weight unless otherwise specified.

As used herein, the term "mammal" includes a human.

It will be appreciated by those skilled in the art that reference herein to treatment extends to prophylaxis as well as the treatment of established diseases or symptoms.

Moreover, it will be appreciated that the amount of a compound of the invention required for use in treatment will vary with the nature of the condition being treated and the age and the condition of the patient and will be ultimately at the discretion of the attendant physician. In one aspect of the invention, the compound is administered in a daily dose of about 30 mg/kg of the body weight to about 300 mg/kg of the body weight, to a human in need thereof. The daily dose for a non-human mammal would be the same. The desired dose may conveniently be presented in a single dose or as divided doses administered at appropriate intervals, for example as two, three, four or more sub-doses per day.

The term "dosage form" refers to physically discrete units suitable as unit dosage forms for mammals such as humans. Each dosage form contains a predetermined quantity of active materials calculated to produce the desired therapeutic effect, in association with a suitable pharmaceutical carrier.

The compositions according to the invention may contain between 0.1-99% of the active ingredient, conveniently from 30-95% for tablets and capsules and 3-50% for liquid preparations.

As used herein, the term "pharmaceutically acceptable carrier" means a non-toxic, inert, solid, semi-solid, diluent, encapsulating material or formulation auxiliary of any type. Some examples of materials which can serve as pharmaceutically acceptable carriers are sugars such as lactose, glucose, and sucrose; starches such as corn starch and potato starch; cellulose and its derivatives such as sodium carboxymethyl cellulose, ethyl cellulose and cellulose acetate; malt; gelatin; talc; as well as other non-toxic compatible lubricants such as sodium lauryl sulfate and magnesium stearate, as well as coloring agents, releasing agents, coating agents, sweetening, flavoring and perfuming agents; preservatives and antioxidants can also be present in the composition, according to the judgment of the formulator.

In addition to the active ingredient and carrier substances, the pharmaceutical compositions may contain additives such as, for example, fillers, antioxidants, dispersants, emulsifiers, defoamers, flavors, preservatives, solubilizers or colorants.

In one aspect of the invention of the present invention, the additive may be selected from a group consisting of nutrients such as proteins, carbohydrates, sugars, talc, magnesium stearate, cellulose, calcium carbonate, starch-gelatin paste and/or pharmaceutically acceptable carriers, excipients, diluents or solvents.

In another aspect of the invention of the present invention, the composition is administered through known routes of administration such as oral, intravenous, intramuscular or subcutaneous routes to a mammal such as a human suffering from said malignancies or chronic arthritis including rheumatoid arthritis, or allergy which may be characterised by activation of NF-KB pathway and/or elevated levels of inflammatory cytokines.

In an aspect of the invention, the treatment methods and methods for reducing cellular proliferation described herein include the administration of pharmaceutical compositions described above, by known administration routes, modes, etc. including the following.

The composition can be administered orally, for example in the form of pills, tablets, coated tablets, capsules, granules, elixirs or syrup. The pharmaceutical composition may be in the forms normally employed, such as tablets, lozenges, capsules, powders, syrups, solutions, suspensions and the like specially formulated for oral, buccal, parenteral, transdermal, inhalation, intranasal, transmucosal, implant, or rectal administration. For buccal administration, the formulation may take the form of tablets or lozenges formulated in conventional manner. Tablets and capsules for oral administration may contain conventional excipients such as binding agents, (for example, acacia, gelatin, sorbitol, tragacanth, mucilage—of starch or polyvinylpyrrolidone), fillers (for example, lactose, sugar, microcrystalline cellulose, maize-starch, calcium phosphate or sorbitol), lubricants (for example, magnesium stearate, stearic acid, talc, polyethylene glycol or silica), disintegrants (for example, potato starch or sodium starch glycolate) or wetting agents, such as sodium lauryl sulfate. The tablets may be coated according to methods well known in the art.

Alternatively, the compounds of the present invention may be incorporated into oral liquid preparations such as aqueous or oily suspensions, solutions, emulsions, syrups or elixirs. Moreover, formulations containing these compounds may be presented as a dry product for constitution with water or other suitable vehicle before use. Such liquid preparations may contain conventional additives such as suspending agents such as sorbitol syrup, methyl cellulose, glucose/sugar syrup, gelatin, hydroxyethylcellulose, carboxymethyl cellulose, aluminum stearate gel or hydrogenated edible fats; emulsifying agents such as lecithin, sorbitan mono-oleate or acacia; non-aqueous vehicles (which may include edible oils) such as almond oil, fractionated coconut oil, oily esters, propylene glycol or ethyl alcohol; and preservatives such as methyl or propyl p-hydroxybenzoates or sorbic acid. Such preparations may also be formulated as suppositories, e.g., containing conventional suppository bases such as cocoa butter or other glycerides.

Additionally, formulations of the present invention may be formulated for parenteral administration by injection or continuous infusion. Formulations for injection may take such forms as suspensions, solutions, or emulsions in oily or aqueous vehicles, and may contain formulatory agents such as suspending, stabilizing and/or dispersing agents.

Alternatively, the active ingredient may be in powder form for constitution with a suitable vehicle (e.g., sterile, pyrogen-free water) before use.

In yet another aspect of the invention, the compound of general formula 1 or a composition containing such compound inhibits the growth of lymphoid leukemia cell line Molt-4.

In another aspect of the invention, the compound of general formula 1 or a composition containing such compound inhibits the growth of acute myeloid leukemia cell line U937.

In yet another aspect of the invention, the compound of general formula 1 or a composition containing such compound inhibits the growth of another acute myeloid leukemia cell line HL-60.

In another aspect of the invention, the compound of general formula 1 or a composition containing such compound inhibits the growth of chronic myeloid leukemic cell line K562.

In yet another aspect of the invention, the compound of general formula 1 or a composition containing such compound inhibits the growth of another chronic myeloid leukemia cell line KU812.

In another aspect of the invention, the compound of general formula 1 or a composition containing such compound inhibits the growth of prostate cancer cell line PC3.

In yet another aspect of the invention, the compound of general formula 1 or a composition containing such compound inhibits the growth of breast cancer cell line MCF-7 of epithelial origin.

In another aspect of the invention, the compound of general formula 1 or a composition containing such compound inhibits the growth of pancreatic cancer cell line MIA PaCa-2.

In yet another aspect of the invention, most compounds of general formula 1 or their compositions do not affect the viability of normal human peripheral blood mononuclear cells (PBMC).

In another aspect of the invention, the compound of general formula 1 or a composition containing such compound induces apoptosis and necrosis of acute myeloid leukemia cell line U937.

In yet another aspect of the invention, the compound of general formula 1 or a composition containing such compound inhibits the growth of Ehrlich ascites carcinoma of epithelial origin in vivo.

In a further aspect of the invention, the compound of general formula 1 or a composition containing such compound exhibits in vivo efficacy in breast carcinoma (MCF-7) model.

DMAP: 4-(N,N-dimethyl)aminopyridine
DTT: dithiothreitol
EGTA: ethylene glycol tetraacetic acid
HCl.NH$_2$NHPh: phenyl hydrazine hydrochloride
HEPES: 4-(2-hydroxyethyl)-1-piperazineethanesulfonic acid The compounds were characterized by comparison of the spectral data obtained with literature data available.

Melting points were recorded on a SPAC-N-SERVICE (India) open capillary melting point apparatus and are uncorrected.

NMR spectra were recorded on a Bruker DPX 300 MHz and Bruker DRX 600 MHz NMR instrument at room temperature and making a solution of samples in CDCl$_3$ or DMSO-d6 solvent using tetramethylsilane (TMS) as the internal standard and are given in the δ (parts per million) scale. The peak shapes are denoted as follows: s, singlet; d, doublet; t, triplet; q, quartet; m, multiplet; dd, double doublet; br s, broad singlet.

Mass spectra, ESI and GCMS were recorded in a Micro mass Q-TOF Micro™ spectrometer and SHIMADZU GCMS-QP5050A GAS CHROMATOGRAPH MASS SPECROMETER using ZB-5 capillary column respectively. Mass spectral data, correspond to ESIMS or GCMS are given in m/z unit.

Infrared spectra were recorded on a JASCO-FT-IR Model-410. Spectra were calibrated against the polystyrene absorption at 1601 cm-1. Samples were scanned in neat or KBr discs.

Analytical thin layer chromatography (TLC) was performed on standard Merck TLC silica gel 60 F254 aluminum sheets. Visualization of the spots on TLC plate was achieved either by exposure to iodine vapor or UV light. All reactions were monitored by employing TLC technique. Column chromatography was carried out on a silica gel 60-120 mesh.

All evaporation of solvents was carried out under reduced pressure on a EYELA Aspirator A-3S with EYELA Cool ACE-1111.

EXAMPLES

The present invention will be more specifically explained by following examples. However, the scope of the present invention is not limited to the scope of these examples below.

Example 1

Collection of Plant Material

The leaves of Piper betle were collected from different areas of West Bengal, India. A voucher specimen was deposited at the Department of Medicinal Chemistry at the Indian Institute of Chemical Biology, Kolkata, India.

Example 2

Purification of Compound No. 1 From Piper Betle Leaves

Fresh leaves of Piper betle (5 kg) were collected, cut into small pieces, and homogenized with 4.0 liter of methanol in a blender. The homogenate was kept for 48 hours in a percolator and then it was passed through fine cheesecloth to filter out the large particles. The fine suspended particles in filtrate were removed by filtering through filter paper. The clear solution of methanol extract was evaporated to dryness under reduced pressure. All the solid particles were collected in the percolator and extraction was repeated with methanol two more times following the above method to get maximum yield. The combined methanol extract was dried to a semi-solid mass (106 g).

The methanol extract was partitioned between ethyl acetate and water. The aqueous layer was further extracted with n-butanol. Removal of the solvent in vacuo from ethyl acetate-soluble portion, n-butanol-soluble and aqueous phase yielded 46 g, 10.4 g and 50.1 g of fraction respectively. The ethyl acetate fraction (21 g) was subjected to silica gel chromatography with petroleum ether, chloroform-petroleum ether (1:1), chloroform-petroleum ether (9:1) and chloroform as eluants. Each eluant was evaporated to dryness and the residue was tested for bioactivity in various cancer cell-lines. The activity was found in the residue obtained from chloroform-petroleum ether (9:1) eluant (2.9 g). Rechromatography of this residue over silica gel using the same procedure furnished a pure compound (1.4 g) identified as hydroxychavicol (Compound No. 1), m.p. 48-49° C.

IR (Neat) cm$^{-1}$: 3360, 1607, 1519, 1441, 1281, 1110 and 913

$^1$H NMR (600 MHz, CDCl$_3$): δ 3.27 (d, 2H, J=7.2 Hz), 5.03-5.10 (m, 2H), 5.19 (brs, 2H), 5.89-5.95 (m, 1H), 6.63 (dd, J=1.8, 4.8 Hz, 1H), 6.71 (d, J=1.8 Hz, 1H), 6.79 (d, J=7.8 Hz, 1H).

$^{13}$C NMR (125 MHz, CDCl$_3$): δ 39.49, 115.32, 115.59, 115.67, 121.00, 133.24, 137.60, 141.64, 143.42.

MS (EI) m/z: 150 (M$^+$), 131,123,103, 77 and 51

Example 3

Preparation of Compound 1 and 16

Step 1) Preparation of Compound B-(2-(allyloxy) phenol

To a solution of pyrocatechol (Compound A) (5 g, 0.045 mol) in dry acetone (20 mL) was added dry potassium carbonate (K$_2$CO$_3$) (6.36 g, 0.044 mol) in portions for 30 minutes. The reaction mixture was stirred at room temperature for 1 hour. Allyl bromide (3.84 mL, 0.045 mol) was then added to the above mixture over 30 minutes. The reaction mixture was refluxed at 60-70° C. for 5 hours. After completion of the reaction, K$_2$CO$_3$ was filtered off. The filtrate was concentrated and extracted with chloroform (3×75 mL), washed with brine (1×50 mL) and dried over anhydrous sodium sulfate. The crude material was purified by column chromatography over silica gel (silica gel; 60-120 mesh) using increasing concentration of chloroform in petroleum ether. Eluants of 4% chloroform in petroleum ether, on concentration, yielded pure Compound B as a thick orange coloured liquid.

Yield: 5.8 g (85%),
$^1$H NMR (300 MHz, CDCl$_3$): δ 4.59 (d, J=4.29 Hz, 2H,) 5.35 (qt, J=17.2, 10.46 Hz, 2H,), 5.69 (s, 1H), 6.04-6.08 (m, 1H) 6.81-6.96 (m, 4H).

Mass (ESI) m/z: 149 [M−H]$^-$

Step 2) Preparation of Compound 1 and 16

The compound B (5 g, 0.033 mol) was heated at 170° C. temperature for 2 hours under N$_2$ atmosphere. After completion of the reaction, the crude reaction mixture was purified by column chromatography (silica gel: 60-120) using petroleum ether with increasing concentration of chloroform. The pure compounds corresponding to Compound No. 16 and Compound No. 1 were eluted with 45% and 75% chloroform in petroleum ether respectively.

Compound 1
Yield: 900 mg (18%); White solid
M. P.: 40-45° C.,
$^1$H NMR (600MHz, CDCl$_3$): δ 3.27 (d, 2H, J=7.2 Hz), 5.03-5.10 (m, 2H), 5.19 (brs, 2H), 5.89-5.95 (m, 1H), 6.63 (dd, J=1.8, 4.8 Hz, 1H), 6.71 (d, J=1.8 Hz, 1H), 6.79 (d, J=7.8 Hz, 1H).

$^{13}$C NMR (125 MHz, CDCl$_3$): δ 39.49, 115.32, 115.59, 115.67, 121.00, 133.24, 137.60, 141.64, 143.42.

GCMS m/z:150 [M$^+$, 100%]

Compound 16
Yield: 2.7 g (54%); Colourless liquid
$^1$H NMR (600 MHz, CDCl$_3$): δ 3.42 (d, J=6 Hz, 2H), 5.15-5.20 (m, 2H), 5.31 (s, 1H, —OH), 5.45 (s, 1H, —OH), 5.99-6.1 (m, 1H), 6.67-6.78 (m, 3H), $^{13}$C NMR (125 MHz, CDCl$_3$): δ 35.04, 113.61, 116.50, 120.98, 125.88, 136.45, 141.98, and 143.96.

GCMS m/z: 150 [M$^+$, 100%]

Example 4

Preparation of Compound 4 and Compound 17

Step 1) Preparation of Compound C (4-propylbenzene-1,2-diol)

To a solution of Compound No. 1 (5 g, 0.033 mol) as obtained in Example 3, in dry methanol (30 mL) was added 10% Pd-charcoal (750 mg, 1.5 eq.). The reaction mixture was stirred at room temperature for 2 hours. After complete disappearance of the starting material, the reaction mixture was filtered over a bed of Celite using methanol. The filtrate was concentrated and purified by column chromatography (silica gel: 60-120 mesh) using petroleum ether with increasing proportion of chloroform. The eluant of 60% chloroform in petroleum ether, on concentration, gave the desired compound C.

Yield: 4.8 g (95%); Colourless liquid
$^1$H NMR (300 MHz, CDCl$_3$): δ 0.98 (t, J=7.31 Hz, 3H), 1.58-1.72 (m, 2H), 2.58 (t, J=7.64 Hz, 2H), 5.05 (brs, 2H), 6.60 (d, J=6.62 Hz, 1H), 6.67 (d, J=6.69 Hz, 1H), 6.75 (s, 11H).

GCMS m/z: 152 [M$^+$, 100%]

Step 2) Preparation of Compound 4 and 17

Compound C (1 g, 0.0066 mol) and dry acetone (15 mL) were stirred for 30 minutes and then dry K$_2$CO$_3$ (0.832 g, 0.0059 mol) was added in portions for 30 minutes The stirring was continued for another hour. Allyl bromide (0.499 mL, 0.0058 mol) was then added to the mixture for 30 minutes. The reaction mixture was refluxed for 5 hours. After completion of the reaction, the reaction mixture was filtered. The filtrate was concentrated and extracted with chloroform (3×50 mL), washed with brine (1×50 mL) and dried over anhydrous sodium sulfate. The solvent was then removed under reduced pressure. The crude material was heated at 175-180° C. for 2 hours. After complete disappearance of the starting material, the reaction mixture was purified by column chromatography (silica gel: 60-120 mesh) using petroleum ether with increasing concentration of chloroform. The pure compounds corresponding to Compound No. 17 and Compound No. 4 were eluted at 25% and 45% chloroform in petroleum ether respectively.

Compound 4

Yield: 200 mg (15%); colourless liquid $^1$H NMR (300 MHz, CDCl$_3$,): δ 0.97 (t, J=7.24 Hz, 3H), 1.57-1.67 (m, 2H), 2.54 (t, J=7.82 Hz, 2H), 3.39 (d, J=6.18 Hz, 2H), 4.9-5.39 (m, 4H), 5.9-6.07 (m, 1H), 6.60 (s, 1H), 6.65 (s, Hz, 1H).

Mass (ESI) m/z 191 [M–H]$^-$

Compound 17

Yield: 260 mg (20.58%); light yellow liquid.

$^1$H NMR (300 MHz, CDCl$_3$): δ 0.97 (t, J=7.22 Hz, 3H), 1.59-1.67 (m, 2H), 2.57 (t, J=7.54 Hz, 2H), 3.31 (d, J=5.94 Hz, 2H), 5.01 (d, J=8.0, 2H), 5.35 (s, 1H), 5.59 (s, 1H), 5.88-5.9 (m, 1H), 6.59 (d, J=7.54 Hz, 1H), 6.66 (d, J=7.54 Hz, 1H).

Mass (ESI) m/z: 191 [M–H]$^-$

Example 5

Preparation of Compound No. 18

Compound No. 4 (0.100 g, 0.00052 mol) as obtained in Example 4, and dry acetone (5 mL) were stirred for 30 minutes and then dry K$_2$CO$_3$ (0.065 g, 0.000468 mol) was added in portions for 30 minutes. The stirring was continued for another hour. Allyl bromide (0.04 mL, 0.000468 mol) was added to the mixture over a period of 30 minutes. Then the reaction mixture was refluxed for 5 hours. After completion of the reaction, the reaction mixture was filtered. The filtrate was concentrated, extracted with chloroform (3×10 mL), washed with brine (1×10 mL) and dried over anhydrous sodium sulfate. The solvent was removed under reduced pressure. The crude material was heated at 175-180° C. for 2 hours. The reaction mixture was cooled to room temperature and purified by column chromatography (silica gel: 60-120 mesh) using petroleum ether with increasing proportion of chloroform. The eluant of 25% chloroform in petroleum ether, on concentration, afforded pure compound corresponding to Compound No. 18 as a colourless liquid.

Yield: 27 mg (22.4%); colourless liquid.

$^1$H NMR (300MHz, CDCl$_3$): δ 0.94 (t, J=7.29 Hz, 3H), 1.45-1.56 (m, 2H), 2.51 (t, J=7.98 Hz, 2H), 3.26 (d, J=7.1, 2H) 3.29 (d, J=7.3, 2H), 5.01-5.31 (m, 6H). 5.90 6.1 (m, 2H), 6.51 (s, 1H).

Mass (ESI) m/z: 231 [M–H]$^-$

Example 6

Preparation of Compound 2 and 3

To a solution of pyrocatechol (Compound A) (1 g, 0.009 mol) and dry acetone (10 mL) was added dry K$_2$CO$_3$ (2.646 g, 0.0189 mol) in portions for 30 minutes. The stirring was continued for another hour. Allyl bromide (1.6 mL, 0.0189 mol) was added to the mixture for 30 minutes and the mixture was refluxed for 5 hours. After completion of the reaction, the solid was filtered and filtrate was concentrated and extracted with chloroform (3×50 mL), washed with brine (1×50 mL), dried over anhydrous sodium sulfate and solvent was removed under reduced pressure. The crude material was heated at 175-180° C. for 2 hours. The reaction mixture was purified by column chromatography (silica gel: 60-120 mesh) using petroleum ether with increasing concentration of chloroform. Elution of 60% and 75% chloroform in petroleum ether yielded pure compounds corresponding to Compound No. 2 and Compound No. 3 as liquids respectively.

Compound 2

Yield: 220 mg (12.86%); light yellow liquid $^1$H NMR (300MHz, CDCl$_3$): δ 3.21 (d, 4H, J=6.21 Hz), 5.01-5.08 (m, 4H), 5.15 (brs, 2H), 5.81-5.92 (m, 2H), 6.76 (s, 2H).

$^{13}$C NMR (75Hz, CDCl$_3$): δ 35.28 (2C), 116.64 (2C), 121.83 (2C), 124.48 (2C), 137.06 (2C), 142.66 (2C).

Mass (ESI) m/z: 189 [M–H]$^-$

Compound 3

Yield: 140 mg (8.18%); brown liquid.

$^1$H NMR (300 MHz, CDCl$_3$): δ 3.30 (d, 2H, J=6.13 Hz), 3.42 (d, J=5.82 Hz, 2H), 4.98-5.12 (m, 6H), 5.91-5.99 (m, 2H), 6.64 (s, 1H), 6.73 (s, 1H).

Mass (ESI) m/z: 189 [M–H]$^-$

Example 7

Preparation of Compound 5, 6, 7, 8, 19, 20 and 21

To a solution of Compound No. 16 (1 g, 0.0066 mol) as obtained in Example 3, in dry pyridine (4 mL) was added acetyl chloride (1.05 mL, 0.0146 mol) under ice-cold conditions for 30 minutes. The reaction mixture was heated at 60-70° C. for 4 hours. After completion of the reaction, the solvent was removed under reduced pressure using rotary evaporator to leave a solid mass. The crude product was purified by column chromatography over silica gel (60-120 mesh) using petroleum ether with increasing proportion of chloroform. Eluant of 20% chloroform in petroleum ether yielded Compound No. 19 as white powder. This was further crystallized from chloroform in petroleum ether.

Spectral data of compounds corresponding to Compound No. 7 and Compound No. 19 are given below as representative data:

Compound 7 Yield: 0.86 g (55%), colourless liquid.

$^1$H NMR (300 MHz, CDCl$_3$): δ 2.18(s, 3H), 2.24(s, 3H), 3.36 (d, J=6.6Hz, 2H), 5.09 (d, J=13.4, 2H), 5.85-5.97(m, 1H), 6.99(s, 1H), 7.10(d, J=14Hz, 2H).

$^{13}$C NMR (75 MHz, CDCl$_3$): δ 20.32(2C), 39.18, 116.37, 122.92, 123.14, 126.39, 136.20, 138.65, 140.08, 141.69, 168.03, 168.12.

GCMS m/z: 234 (M$^+$, 100%)

Compound 19 Yield: 0.7 g (45%), white powder m.p.: 58-60° C.

$^1$H NMR (300 MHz, CDCl$_3$): δ 2.27 (s, 3H), 2.29 (s, 3H), 3.34 (d, J =6.49Hz, 2H), 5.08 (d, J=12.45 Hz, 2H), 5.80-5.95 (m, 1H), 7.05-7.24 (m, 3H).

$^{13}$C NMR (75 MHz, CDCl$_3$): δ 20.29, 20.62, 34.51, 116.56, 121.39, 126.28, 127.42, 134.01, 135.31, 140.61, 142.51, 167.99, and 168.29.

GCMS m/z: 234 [M]$^+$

Example 8

Preparation of Compound No. 9

Step 1) Preparation of Methyl 1,3-benzodioxol-5-yl acetate (Compound E):

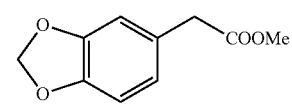

E

A solution of commercially available 3,4-(methylenedioxy)-phenyl acetic acid (Compound D) (5.00 g, 27.75 mmol) in methanol (20 mL) was cooled at 0° C. and thionyl chloride (2.5 mL, 28.85 mmol) added drop wise and the reaction mixture was stirred for 30 minutes. The reaction mixture was evaporated to dryness, diluted with ethyl acetate and washed with saturated, aqueous NaHCO₃ and water respectively. The organic layer was dried over anhydrous sodium sulfate, filtered and then concentrated. Purification on silica gel using 6:1 petroleum ether-ethyl acetate as eluant afforded Compound E (5.00 g, 93%) as a colourless oil.

$^1$H NMR (600 MHz, CDCl₃): δ 6.78-6.70 (m, 3H, aromatic protons), 5.94 (s, 2H, OCH₂O), 3.69 (s, 3H CO₂CH₃), 3.54 (s, 2H, CH₂CO₂CH₃).

Step 2) Preparation of Methyl 2-(1,3-benzodioxol-5-yl) propanoate (Compound F)

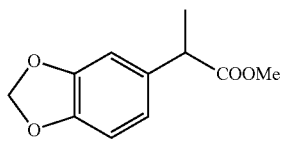

F

To a solution of diisopropylamine (3.46 mL, 24.78 mmol) in tetrahydrofuran (15 mL) at 0° C., n-BuLi (1.6 M in hexane) (15.45 mL, 24.66 mmol) was added dropwise under N₂ atmosphere. The solution was stirred at 0° C. for 30 minutes and then cooled to −78° C. A solution of Compound E (4.00 g, 20.59 mmol) in tetrahydrofuran (15 mL) was then added dropwise. The reaction mixture was stirred at −78° C. for 2 hours and then CH₃I (6.4 mL, 102.99 mmol) was added dropwise. The resulting mixture was stirred overnight at −78° C. The reaction was quenched with saturated, aqueous NH₄Cl solution and was allowed to attain room temperature. The solution was diluted with diethyl ether and washed with distilled water. The organic layer was dried over anhydrous sodium sulfate, filtered and concentrated. Purification on silica gel column using 12:1 petroleum ether-ethyl acetate as eluant yielded Compound F (4.00 g, 77.6%) as a light yellow oil.

$^1$H NMR (600 MHz, CDCl₃): δ 6.81-6.74 (m, 3 H, aromatic protons), 5.94 (s, 2 H, OCH₂O), 3.66 (s, 3 H, CO₂CH₃), 3.64 (q, 1H, CHCH₃, J=7.2 Hz), 1.46 (d, 3 H, CH₃, J=7.2 Hz)

Step 3) Preparation of Methyl 2-(1,3-benzodioxol-5-yl)-2-methyl propanoate (Compound G)

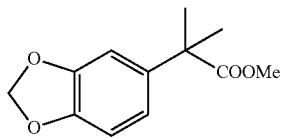

G

Compound F (4.26 g, 20.46 mmol) was treated with LDA (lithium diisopropylamide) and CH₃I in dry tetrahydrofuran under the similar condition as described for the preparation of compound 6 to obtain Compound G. After purification on silica gel column using 12:1 petroleum ether-ethyl acetate as eluant afforded the desired compound G (4.34 g, 95%) as a yellow oil.

$^1$H NMR (600 MHz, (CDCl₃): δ 6.84-6.75 (m, 3 H, aromatic protons), 5.94 (s, 2 H, OCH₂O), 3.65 (s, 3 H, CO₂CH₃), 1.55, 1.54 (2 s, 6H, 2 CH₃).

Step 4) Preparation of 2-(1,3-benzodioxol-5-yl)-2-methyl propan-1-ol (Compound H)

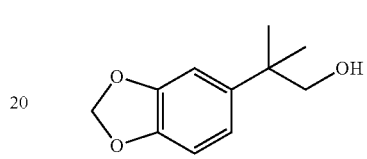

H

The solution of Compound G (3.94 g, 17.73 mmol) in dry tetrahydrofuran (15 mL) was added dropwise to an ice cooled (0° C.) suspension of LiAlH₄ (740 mg, 19.50 mmol) in dry tetrahydrofuran (15 mL). After completion of addition, the reaction mixture was stirred at 0° C. for 30 minutes and then at room temperature for additional 2 hours. It was then cooled to 0° C. and a saturated aqueous solution of sodium sulfate added dropwise. The reaction mixture was further stirred for 30 minutes to destroy excess LiAlH₄, filtered, washed with diethyl ether and obtained Compound H as a white solid (3 g, 87%).

$^1$H NMR (300 MHz, CDCl₃): δ 6.89-6.76 (m, 3 H, aromatic protons), 5.94 (s, 2 H, OCH₂O), 3.56 (s, 2 H, CH₂OH), 1.29 (s, 6H, 2 CH₃).

Step 5) Preparation of 2-(1,3-benzodioxol-5-yl)-2-methyl propanal (Compound I)

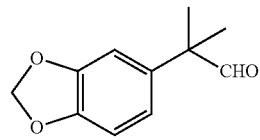

I

A suspension of 3A° molecular sieves (6.5 g) in CH₂Cl₂ (15 mL) was stirred at room temperature for 30 minutes and then PCC (pyridinium chlorochromate) (2 g) was added. To this PCC suspension, a solution of Compound H (1 g, 5.15 mmol) in dry CH₂Cl₂ (15 mL) was added dropwise and was stirred at room temperature for 3.5 hours.

The reaction mixture was evaporated to dryness and purified by silica gel column. Elution with diethyl ether afforded desired Compound I (700 mg, 71%) as light yellow oil.

$^1$H NMR (300 MHz, CDCl₃): δ 9.43 (s, 1 H, CHO), 6.82-6.72 (m, 3 H, aromatic protons), 5.96 (s, 2 H, OCH₂O), 1.56 (s, 6H, 2 CH₃).

Step 6) Preparation of 2-(1,3-benzodioxol-5-yl)-2-methyl propanal oxime (Compound J)

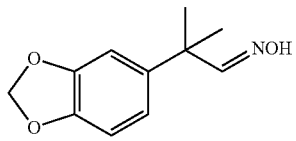

To a solution of Compound I (511 mg, 2.66 mmol) in ethanol (1 mL), HCl.NH$_2$OH (277 mg, 4.00 mmol) and pyridine (2.2 mL, 26.58 mmol) were added and it was stirred at room temperature for 1.5 hours. The reaction mixture was evaporated to dryness and added 10 mL of ethyl acetate. The organic layer was washed with distilled water, dried over anhydrous sodium sulfate, filtered and evaporated. The crude reaction mixture was purified over silica gel column using 5:1 petroleum ether-ethyl acetate as solvent to afford Compound J (528 mg, 96%) as a white foam.

$^1$H NMR (300 MHz, CDCl$_3$): δ 7.44 (s, 1 H, CH=NOH), 6.82-6.77 (m, 3 H, aromatic protons), 5.94 (s, 2 H, OCH$_2$O), 1.45 (s, 6 H, 2 CH$_3$).

Step 7) Preparation of Compound No. 9

To a suspension of anhydrous AlCl$_3$ (193 mg, 1.45 mmol) in dry CH$_2$Cl$_2$ (1 mL), a solution of Compound J (60 mg, 0.29 mmol) in dry CH$_2$Cl$_2$ (1 mL) was added drop-wise at room temperature under N$_2$ atmosphere and stirred at the same temperature for 3 hours. The reaction mixture was cooled to 0° C., 20 μL of cold distilled water was added, the reaction mixture was allowed to attain room temperature and stirred for 12 hours at the same temperature under N$_2$ atmosphere. The reaction mixture was evaporated to dryness and triturated several times with 2:1 ethyl acetate-CH$_2$Cl$_2$ and followed by 10:1 ethyl acetate-methanol. The organic solutions were combined and evaporated to dryness. The crude material was purified by preparative thin-layer chromatography using 2:1 petroleum ether-ethyl acetate to obtain the desired Compound No. 9 (30 mg, 53%) as white foam.

$^1$H NMR (300 MHz, CD$_3$OD): δ 7.36 (s, 1 H, CH=NOH), 6.77-6.62 (m, 3 H, aromatic protons), 1.40 (s, 6 H 2 CH$_3$). $^{13}$C NMR (75 MHz)

$^{13}$C NMR (75 MHz, CD$_3$OD): δ 158.75 (CH=NOH), 146.11, 144.75, 139.26, 118.23, 116.20, 114.60 (aromatic carbons), 41.09 [>C(CH$_3$)$_2$], 27.32 [>C(CH$_3$)$_2$].

Mass spectrum (EI, m/z) 195 (M)$^+$(C$_{10}$H$_{13}$NO$_3$ requires 195.2).

Example 9

Preparation of Compound 12

A mixture of Compound No. 9 (5 mg, 0.03 mmol), Ac$_2$O (36 μL, 0.39 mmol), catalytic amount of DMAP and pyridine (200 4) was kept at room temperature for 48 hours. The reaction mixture was quenched with 20 μL of cold distilled water, evaporated to dryness and co-evaporated three times 3×200 μL with toluene. The crude reaction mixture was purified over silica gel column using 5:1 petroleum ether-ethyl acetate as solvent to afford Compound No. 12 (5 mg, 52%) as oil.

$^1$H NMR (300 MHz, CDCl$_3$): δ 7.67 (s, 1 H, CH=NOH), 7.26-7.12 (m, 3 H, aromatic protons), 2.31, 2.30, 2.29 (3s, 9H OCOCH$_3$), 1.57 (s, 6H 2 CH$_3$).

$^{13}$C NMR (75 MHz, CDCl$_3$): δ 168.72, 168.29, 168.25 (3 OCOCH$_3$), 163.65 (CH=NOAc), 142.97, 142.07, 140.98, 124.51, 123.56, 121.44 (aromatic carbons), 41.53 [>C(CH$_3$)$_2$], 25.99 [>C(CH$_3$)$_2$], 20.66, 20.61 and 19.59 (3 OCOCH$_3$).

Mass spectrum (ESI, m/z): 344.2 (M+Na)$^+$(C$_{16}$H$_{19}$NO$_6$Na requires 344.2).

Example 10

Preparation of Compound 10

Step 1) Preparation of 1-(2-(benzo[d][1,3]dioxol-5-yl)-2-methylpropylidene)-2-phenylhydrazine (Compound L)

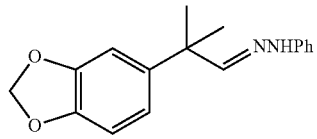

To a solution of Compound I (100 mg, 0.52 mmol) in ethanol (1 mL), HCl.NH$_2$NHPh (90 mg, 0.62 mmol) and NaOAc (85 mg, 1.04 mmol) were added and it was stirred at room temperature for 30 minutes. The reaction mixture was evaporated to dryness and 5 mL of CH$_2$Cl$_2$ added. The organic layer was washed with distilled water, dried over anhydrous sodium sulfate, filtered and evaporated. The crude reaction mixture having more than 95% of hydrazone corresponding to Compound L was used directly in next step, as it was unstable on silica gel. Hydrazone corresponding to Compound L was also confirmed from the mass spectra of the crude mixture.

Step 2) Preparation of Compound 10

On removal of methylenedioxy group of Compound L (50 mg, 0.18 mmol) under similar conditions as described in the preparation of Compound No. 9, the expected dihydroxy hydrazone derivative was not observed. Purification by preparative thin-layer chromatography using 2:1 petroleum ether-ethyl acetate afforded the rearranged cyano compound corresponding to Compound No. 10 (20 mg, 58%) as a reddish oil.

$^1$H NMR (300 MHz, CD$_3$OD): δ 6.92-6.76 (m, 3H, aromatic protons), 1.65 (s, 6H 2 CH$_3$).

$^{13}$C NMR (75 MHz, CD$_3$OD): δ 146.77, 146.14, 134.55, 126.31, 117.42, 116.58, 113.66 (aromatic carbons and —C≡N), 37.80 [>C(CH$_3$)$_2$], 29.71 [>C(CH$_3$)$_2$]

IR (neat) γ$_{max}$: 2242.

Mass spectrum (EI), m/z: 177 (M)$^+$(C$_{10}$H$_{11}$NO$_2$ requires 177.2).

Example 11

Preparation of Compound 13

Step 1) Preparation of Ethyl 4-(1,3-benzodioxol-5-yl)-4-methyl pent-2-enoate (Compound K)

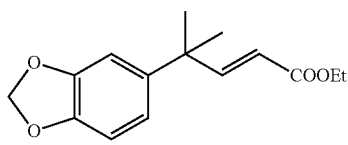

K

To a suspension of 60% NaH (11.2 mg, 0.28 mmol) in dry tetrahydrofuran (0.4 mL) at 0° C., triethyl phosphonoacetate (TEPA) (60 µL, 0.26 mmol) was added. The mixture was allowed to attain room temperature, stirred at the same temperature for 1 hour and again cooled to 0° C. To this mixture at 0° C., a solution of Compound I (30 mg, 0.16 mmol) in dry $CH_2Cl_2$ (0.8 mL) was added drop-wise and stirred at room temperature overnight. The reaction mixture was poured into distilled water (1 mL) and extracted with diethyl ether. The ether layer was dried over anhydrous sodium sulfate, filtered and evaporated. Purification on silica gel column using 20:1 petroleum ether-ethyl acetate afforded Compound K (30 mg, 72%) as a colourless oil.

NMR (300 MHz) ($CDCl_3$): δ 7.07 (d, 1H, J 15.8 Hz, =CHCOOEt), 6.79-6.75 (m, 3H, aromatic protons), 5.93 (s, 2H, $CH_2O$), 5.78 (d, 1H, J 15.8 Hz, >CH=CHCOOEt), 4.19 (q, 2H $CO_2CH_2CH_3$), 1.42 [s, 6H, >C($CH_3$)$_2$], 1.29 (t, 3 H, $CO_2CH_2CH_3$).

Step 2) Preparation of Compound 13

Removal of methylenedioxy group of Compound K (154 mg, 0.587 mmol) was performed under similar conditions as described in the preparation of Compound No. 9.

Purification by preparative thin-layer chromatography using 5:1 petroleum ether-ethyl acetate afforded the desired Compound No. 13 (72 mg, 50%) as reddish oil.

$^1$H NMR (300 MHz, $CDCl_3$): δ 7.08 (d, 1H, J=15.8 Hz, =CHCOOEt), 6.80-6.68 (m, 3H, aromatic protons), 5.78 (d, 1H, 1=15.8 Hz, >CH=CHCOOEt), 5.55 (s, 2H, 2 phenolic-OH), 4.20 (q, 2 H, $CO_2CH_2CH_3$), 1.40 [s, 6H, >C($CH_3$)$_2$], 1.30 (t, 3 H, $CO_2CH_2CH_3$).

$^{13}$C NMR (75 MHz) ($CDCl_3$): δ 168.21 ($CO_2Et$), 158.36 (CH=CHCO$_2$Et), 143.67, 142.23, 139.05 (aromatic carbons), 118.18, 117.25, 115.10, 113.53 (aromatic carbons, CH=CHCO$_2$Et), 60.77 ($CO_2CH_2CH_3$), 40.38 [>C($CH_3$)$_2$], 27.71 [>C($CH_3$)$_2$], 14.10 ($CO_2CH_2CH_3$).

Mass spectrum (EI, m/z): 250 (M)$^+$($C_{14}H_{18}O_4$ requires 250.3).

Example 12

Preparation of Compound 14

A suspension of methyl triphenyl phosphonium bromide (325 mg, 0.95 mmol) and t-BuOK (87.5 mg, 0.78 mmol) in dry tetrahydrofuran (1 mL) was stirred at 0° C. for 1 hour. To this mixture at 0° C., a solution of Compound I (50 mg, 0.26 mmol) in dry tetrahydrofuran (1 mL) was added dropwise. The reaction mixture was stirred at 0° C. for 1 hour and at room temperature for 2 hours and then refluxed for 5 hours. It was then cooled to 0° C. and quenched by $NH_4Cl$ solution with stirring for 30 minutes. The reaction mixture was then extracted with diethyl ether. The ether layer was washed with distilled water, dried over anhydrous sodium sulfate, filtered and evaporated.

Purification on silica gel column using petroleum ether followed by with 20:1 petroleum ether-ethyl acetate afforded desired Compound No. 14 (1 mg) as colourless oil.

$^1$H NMR (300 MHz, $CDCl_3$): δ 6.85-6.72 (m, 3H, aromatic protons), 6.02-5.91 (m, 3H, >CH=$CH_2$, $OCH_2O$), 5.06-5.00 (m, 2H, >CH=$CH_2$), 1.36 [s, 6H, >C($CH_3$)$_2$].

Example 13

Preparation of Compound 11 and 15

A mixture of Compound No. 13 (25 mg, 0.10 mmol) as obtained in Example 11, $Ac_2O$ (0.2 mL, 2.0 mmol), catalytic amount of DMAP and pyridine (0.2 mL) was kept at room temperature for 48 hours. The reaction mixture was quenched with 0.2 mL of cold distilled water, evaporated to dryness and co-evaporated three times 3×0.2 mL with toluene. The crude reaction mixture was purified over silica gel column using 5:1 petroleum ether-ethyl acetate as solvent to afford Compound No. 15 (23 mg, 76%) as oil.

$^1$H NMR (300 MHz, $CDCl_3$): δ 7.26-7.06 (m, 4 H, aromatic protons, =CHCOOEt), 5.83 (d, 1H, J=14.0 Hz, >CH=CHCOOEt), 4.20 (q, 2 H, $CO_2CH_2CH_3$), 2.29, 2.28 (2s, 6 H, $CH_3CO$),1.45 [s, 6 H, >C($CH_3$)$_2$], 1.29 (t, 3 H, $CO_2CH_2CH_3$).

$^{13}$C NMR (75 MHz) ($CDCl_3$): δ 168.21, 168.23, 166.85 (2 $COCH_3$, $CO_2Et$), 156.07 (CH=CHCO$_2$Et), 145.39, 141.74, 140.41, 124.48, 123.13, 121.24, 118.50 (aromatic carbons, CH=CHCO$_2$Et), 60.41 ($CO_2CH_2CH_3$), 40.76 [>C($CH_3$)$_2$], 27.81 [>C($CH_3$)$_2$], 20.65, 20.61 (2 $COCH_3$), 14.22 ($CO_2CH_2CH_3$).

Mass spectrum (EI, m/z): 334 (M)$^+$($C_{18}H_{22}O_6$ requires 334.37).

Example 14

Sensitivity of Compounds 1 and 7 to Spontaneous Autooxidation

Spontaneous autooxidation of compounds having phenolic groups produce reactive oxygen species like $H_2O_2$. The enzyme Catalase breaks down $H_2O_2$ to water, We therefore incubated Compound 1 and 7 (30 □M each) for 30 min and 2 hr in medium alone in the presence and absence of Catalase. Level of $H_2O_2$ in the supernatant was then measured as reported using 3,5,3',5'-tetramethylbenzidine (TMB) reagent (Plant Physiology, 2004, 136, 3114-3123). FIG. 1 represents the data of sensitivity of spontaneous autooxidation of Compound 1 and Compound 7.

Conclusions: Compound 1 undergoes spontaneous autooxidation while Compound 7 is resistant to spontaneous autooxidation.

Example 15

Effects of Compounds of General Formula 1 on Viability of Cancer Cell Lines and Normal Human Peripheral Blood Mononuclear Cells (pbmc) In Vitro Following cancer cell lines were used: chronic myeloid leukemia cell lines K562, KU812; acute myeloid leukemia cell lines HL60, U937; T-lymphoblastic leukemia cell line Molt-4; prostate cancer cell line PC-3; breast cancer cell line MCF-7; pancreatic cancer cell line MIA PaCa-2. These cancer cell lines were maintained in tissue culture in standard growth medium containing 10% heat-inactivated fetal bovine serum (FBS). Normal human peripheral blood mononuclear cells (PBMC) were separated from whole blood by Ficoll/Hypaque density gradient centrifugation. Peripheral blood samples were collected from normal donors with due approval from the Human Ethics Committee of Indian Institute of Chemical Biology, Kolkata, India, and all experiments with human blood were conducted under an approved institutional Human Ethics committee protocol. Informed consent was provided according to the Declaration of Helsinki. Cancer cell lines and PBMC ($5 \times 10^3$) in triplicate were incubated in 0.2 mL of standard growth medium containing 10% FBS with varying concentrations of test compounds of the present invention. After 72 hours of incubation, cells were collected by centrifugation (at 1000 g for 5 minutes) and cell-viability was determined by the trypan blue exclusion assay. At least 200 cells were examined in each sample. Because of monolayer culture, treated and untreated PC-3, MCF-7 and MIA PaCa-2 cells were detached from the wells by treatment with Cell Dissociation Solution (Sigma Chemical, St. Louis, Mo.) before counting. Data are represented as $IC_{50}$ (minimum concentration required to inhibit the viability by 50%) in Table 5.

were stained with Giemsa and viewed under microscope (magnification ×1000). For measurement of apoptosis/necrosis, cells were left untreated or treated with Compound No. 1 (30 µM) or Compound No.7 (15 µM) for 24 hours. After washing, cells were stained with fluorescein isothiocyanate (FITC)-conjugated annexin V and propidium iodide (PI) and analysed in a flow cytometer (BD LSR, Becton Dickinson).

Figure 2:
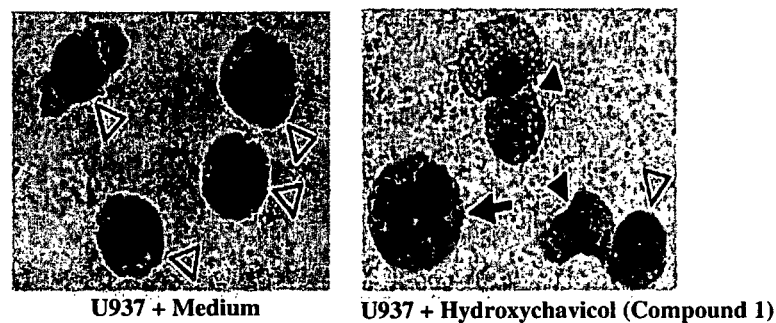
FIG. 2A shows morphology of U937 cells (acute myeloid leukemia cell line) after treatment with regular growth medium alone and regular growth medium containing Compound 1 (hydroxychavicol) (30.0 µM) for 24 hours followed by Giemsa staining
FIG. 2B shows Flow cytometric analysis of apoptosis and necrosis of U937 cells using Compound 1 (hydroxychavicol) and Compound 7 (4-allyl-1,2-phenylene diacetate).
FIG. 2C indicates flow cytometric determination of apoptosis and necrosis of normal human PBMC by Compound 1 (30 µM) and Compound 7 (30 µM) after incubation for 24 hours.
Figure 2:
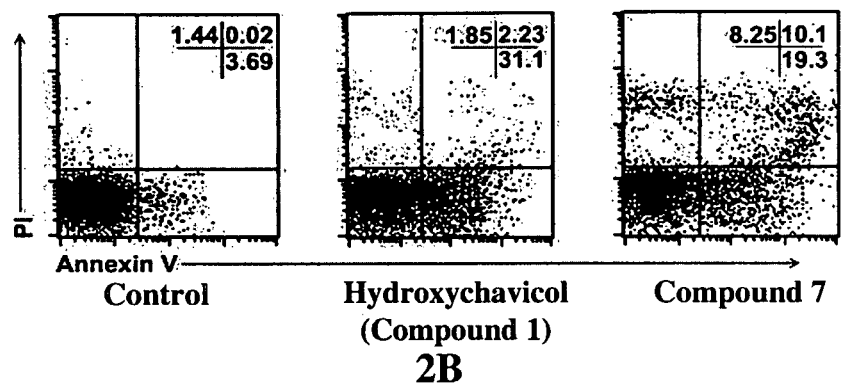
Figure 2:
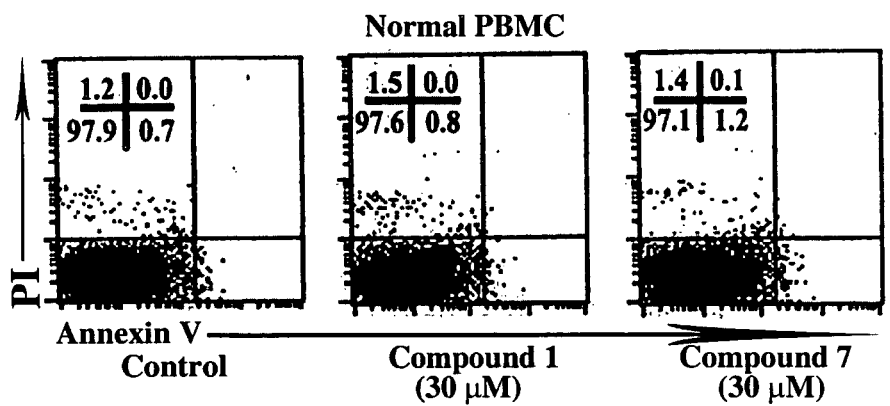

FIG. 2A shows the Morphology of U937 cells after treatment with regular growth medium alone and regular growth medium containing Compound No. 1 (30 µM)) for 24 hours followed by Giemsa staining.

Δ indicates healthy cells; while ▲ indicates necrotic morphology;→indicates apoptotic morphology.

FIG. 2B indicates flow cytometric determination of apoptosis and necrosis by Compound No.1 (hydroxychavicol) and Compound No.7. Apoptosis and necrosis of U937 cells were induced. Cells were left untreated (extreme left panel), or incubated with Compound No.1 (30 µM) (middle panel) or Compound No.7 (extreme right panel) (15 µM) for 24 hours and processed for flow cytometry after staining with annexin V-FITC and propidium iodide (PI). Viable cells are in the lower left quadrant (stained neither by annexin V nor by PI), early apoptotic cells (stained by annexin V only) are in the lower right quadrant, late-stage apoptotic cells (stained by

TABLE 5

In vitro activity of Compounds of general formula 1 against normal human peripheral blood mononuclear cells (PBMC) or cancer cell lines of different origin*
Activity ($IC_{50}$ [µM])

| Compound No | Normal PBMC | Cancer cell lines | | | | | | | |
|---|---|---|---|---|---|---|---|---|---|
| | | K562 | KU812 | HL-60 | U937 | Molt-4 | PC-3 | MCF-7 | MIAPaCa-2 |
| 1** | 80 | 20 | 25 | 25 | 25 | 30 | 35 | 35 | 35 |
| 1 | 80 | 20 | 25 | 25 | 25 | 30 | 35 | 35 | 35 |
| 2 | ND*** | 13 | 25 | 25 | ND | 30 | ND | 40 | ND |
| 3 | 80 | 52 | ND | 60 | ND | 50 | ND | 70 | 70 |
| 7 | 70 | 13 | 15 | 15 | 13 | 15 | 25 | 25 | 30 |
| 9 | 100 | 64 | 70 | 64 | ND | 70 | 80 | 85 | 85 |
| 10 | 150 | 113 | 115 | 110 | 110 | ND | 120 | 100 | 120 |
| 12 | 250 | 194 | 190 | 190 | 190 | 190 | 200 | 200 | ND |
| 13 | 75 | 50 | 45 | 50 | 45 | 45 | 70 | 70 | ND |
| 14 | 800 | 657 | 650 | 670 | 670 | 650 | 670 | 680 | 680 |
| 16 | 30 | 20 | 25 | 20 | 25 | 20 | 30 | ND | ND |
| 19 | 30 | 13 | 20 | 15 | 15 | 20 | 20 | 20 | 20 |

*Cell count assays were performed by plating cells in regular growth medium in the absence and presence of varying concentrations of test compounds of the present invention. Viable cells were counted as assessed by exclusion of trypan blue.
**Isolated from *Piper betle* leaves.
***ND, Not Done Conclusions Certain compounds of the present invention induced killing of cancer cell lines of different origin, for example, chronic myeloid leukemia (K562, KU812), acute myeloid leukemia (HL-60, U937), acute lymphoblastic leukemia (Molt-4), prostate neoplasia (PC-3), breast neoplasia (MCF-7) and pancreatic neoplasia (MIA PaCa-2). Normal human peripheral blood mononuclear cells (PBMC) were used as control.

Example 16

Morphology Analysis and Measurement of Apoptosis/necrosis in U937 Cells after Treatment with Compound No. 1 (4-Allyl-benzene-1,2-diol/hydroxychavicol) and Compound No. 7 (4-allyl-1,2-phenylene diacetate)

U937 cells were treated with standard growth medium alone or with standard growth medium containing hydroxychavicol (30 µM) for 24 hours. Treated and untreated cells both annexin V and PI) are in the upper right quadrant and the necrotic cells (stained by PI only) are in the upper left quadrant.

FIG. 2C indicates flow cytometric determination of apoptosis and necrosis of normal human PBMC by Compound 1 (30 µM) and Compound 7 (30 µM) after incubation for 24 hours.

Conclusions

Microscopic examination indicated that hydroxychavicol-induced killing of U937 cells is due to both apoptosis and necrosis (FIG. 2A). Flowcytometry-based studies after staining with annexin V-FITC/PI indicate that both hydroxychavicol and Compound No.7 induce apoptosis and necrosis (FIG. 2B). In contrast, normal human PBMC remained unaffected by Compound 1 and Compound 7 (FIG. 2C).

Example 17

Effects of Compound 1 and nitric oxide scavenger cPTIO on PI3-Akt pathway

Figure 3:
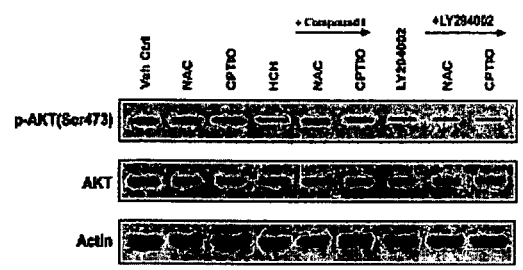
FIG. 3 shows Effect of hydroxychavicol (Compound 1) on the activation of PI3/Akt pathway.

MIA PaCa 2 cells were pretreated with NAC (5 mM), cPTIO (25 μM), PI3K inhibitor LY294002 (10 μM) for 3 hr followed by treatment with Compound 1 (30 μM) for 24 hr. Whole cell lysates were prepared and the phosphorylation status and protein expression of Akt were analyzed by Western blot. Cells were also treated with medium alone, Compound 1 (30 μM), c-PTIO (nitric oxide scavenger; 25 μM) or compound 1 plus c-PTIO for 24 hr. Results of these experiments are shown in FIG. 3.

Conclusions

Compound 1 inhibits the activation of PI3/Akt pathway which is reversed by the nitric oxide scavenger cPTIO. Thus, the effect of Compound 1 is mediated by production of nitric oxide.

Example 18

Transfection with Specific SiRNAs of Nitric Oxide Synthease Isoforms

Figure 4:
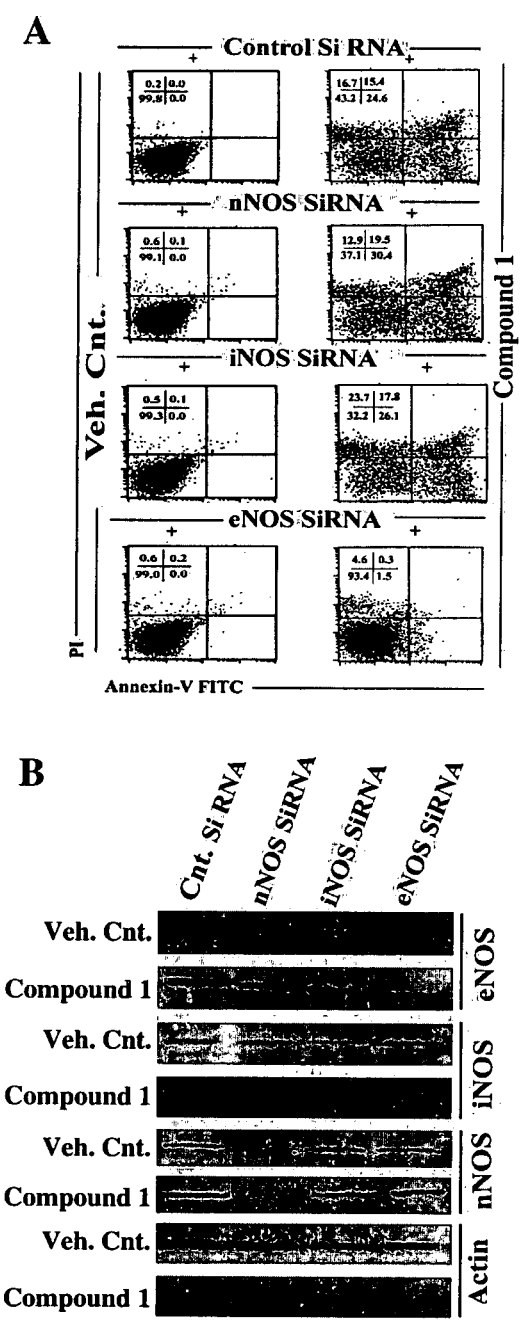
FIG. 4 shows involvement of endothelial nitric oxide synthase (eNOS) in Compound 1 (hydroxy chavicol)-induced apoptosis and nitric oxide production. (A) Effect of transfection with NOS siRNAs on Compound 1-induced apoptosis of MIA PaCa 2 cells (pancreatic cancer cell line). (B) Attenuation of Compound 1-induced upregulatin of eNOS protein in MIA PaCa 2 cells by transfection with eNOS siRNA.

MIA PaCa 2 cells were transfected with control siRNA, nNOS siRNA, iNOS siRNA or eNOS siRNA (purchased from Santa Cruz Biotechnology) for 48 hr. Transfections were carried out following the manufacturer's instructions. The transfection reagent used for siRNA transfection was purchased from Santa Cruz. Cells were then treated with vehicle control or Compound 1 (30 μM) for 24 hr. Apoptosis was analyzed by flow cytometry. Representative dot plots are shown in FIG. 4A. To confirm that transfectin with siRNAs attenuate the protein expression of respective NOS isoforms, Western blot was performed with whole cell lysates. Results are presented in FIG. 4B.

Conclusions

Endothelial nitric oxide synthase (eNOS) is responsible for Compound 1-induced nitric oxide production and cell death.

Example 19

Figure 5:
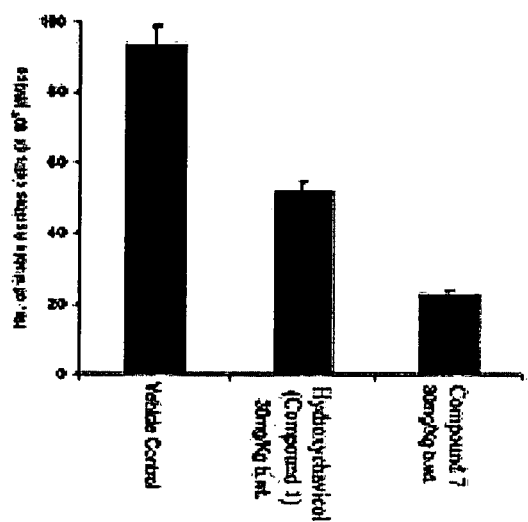
FIG. 5 shows In vivo activity of Compound 1 (hydroxychavicol) and Compound No.7 (4-allyl-1,2-phenylene diacetate) against Ehrlich ascites carcinoma.

In Vivo Efficacy of Compound No.1 (hydroxychavicol) and Compound No.7 (4-allyl-1,2-phenylene diacetate) in Ehrlich Ascites Carcinoma (EAC) Model The in vitro studies indicate that hydroxychavicol and other compounds of the present invention induce killing of a variety of cancer cell lines including breast cancer cell line MCF-7 (Table 5). The MCF-7 cell line is of epithelial origin. Studies were extended in vivo in mouse model for a tumor of epithelial origin. Ehrlich ascites carcinoma is a tumor of epithelial origin (Cancer Research, 1958, 18, 1167-1185). EAC was established in Swiss albino mice as described (Biochemical and Biophysical Research Communications, 2001, 288, 658-665). Swiss albino mice were injected with EAC ($2\times10^6$ cells/mouse) intraperitoneally. 2 days post-injection of tumor cells, these mice (5 per group) were injected intraperitoneally with Compound No. 1 (hydroxychavicol) (30 mg/kg body weight) or Compound No. 7 (30 mg/kg body weight) thrice a week for three weeks. One week after the last injection, mice were sacrificed, and viable cells from peritoneal cavity were counted microscopically. Vehicle (dimethyl sulphoxide [DMSO], 0.1%) was used as control. Results are as indicated in FIG. 5.

Conclusions

Compound No.1 (hydroxychavicol) and Compound No.7 are effective in vivo in destroying EAC tumor of epithelial origin.

Example 20

In Vivo Efficacy Of Compound 1 in Nude Mice Bearing Human Breast Adenocarcinoma Xenograft MCF-7 cells were suspended to $5\times10^7$ cells/ml in Matrigel (BD Biosciences; 1 volume of cells with 1 volume of cold Matrigel). Nude female mice of 6 to 7 weeks of age (National Institute of Nutrition, Hyderabad, India) were injected with 0.2 ml of this cell suspension. Animals were left untreated until MCF-7 xenografts reached 200-300 $mm^3$.

Figure 6:
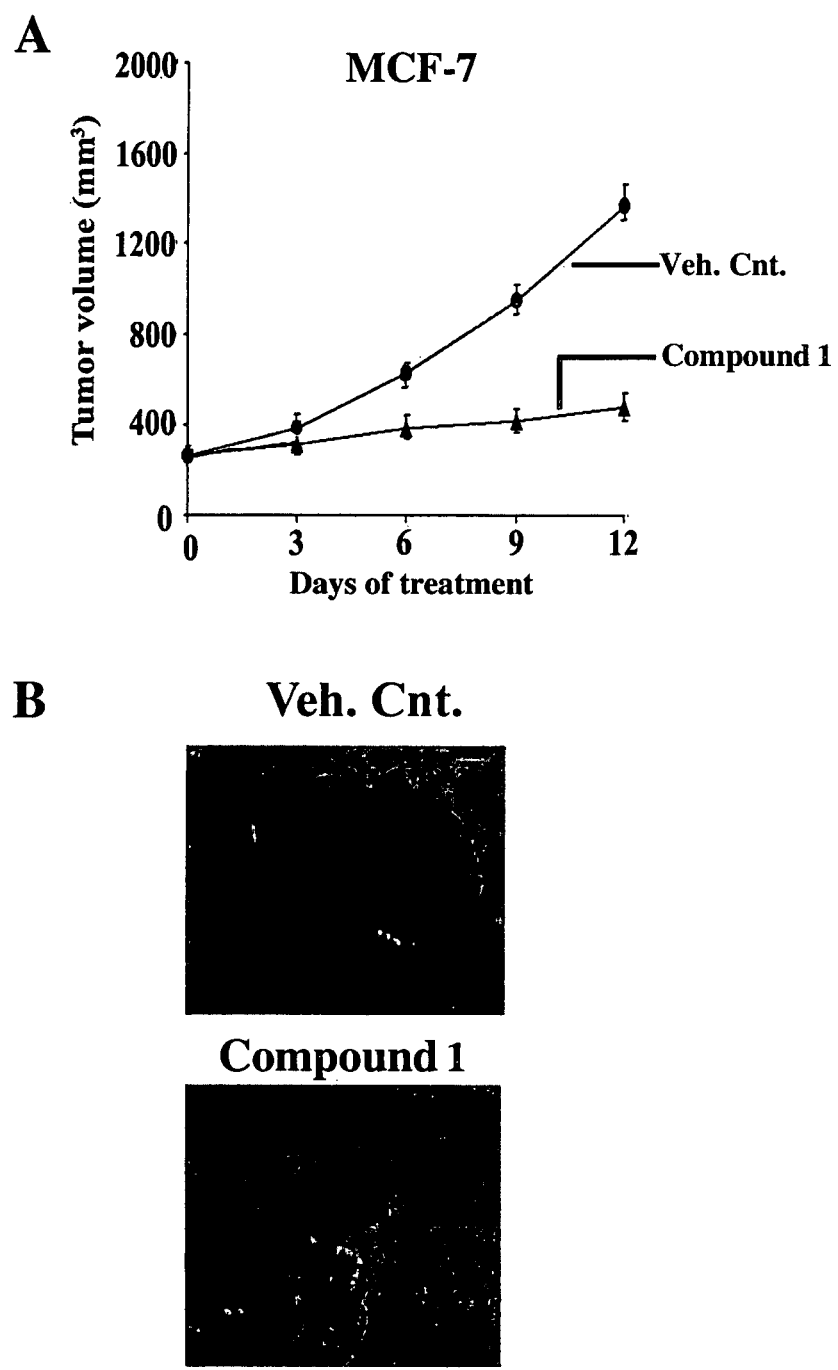
FIG. 6 shows In vivo therapeutic activity of Compound 1 in mice bearing human breast tumor xenograft. (A) MCF-7 cells (breast cancer cell line) embedded in Matrigel were staged in nude mice until tumors reached 200-300 mm$^3$. Veh. control or Compound 1 (100 mg/kg body weight) was administered orally twice a day for 10 days. (B) Representative gross appearance of MCF-7 xenografts after receiving indicated treatments.
Figure 7:
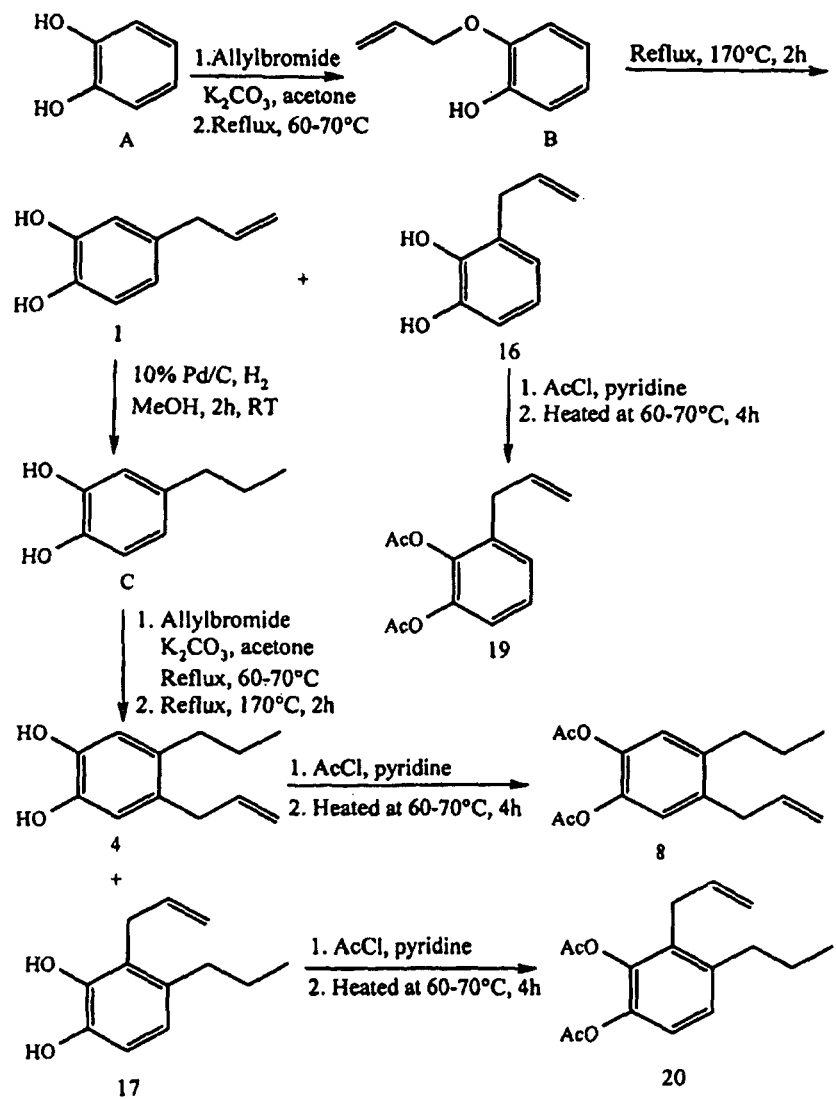
FIG. 7 presents Scheme 1 for the synthesis of certain compounds of general formula 1.
Figure 8:
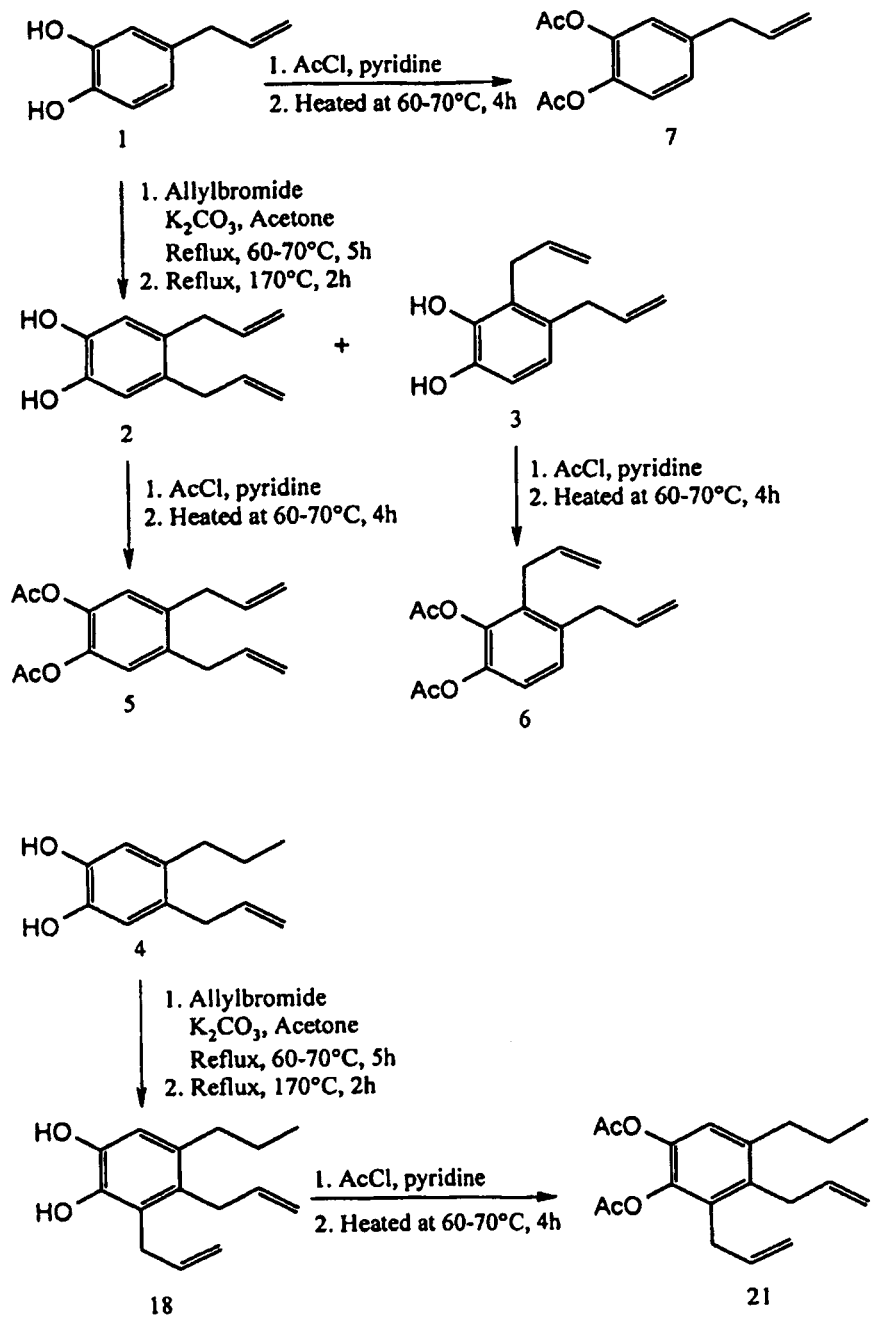
FIG. 8 presents Scheme 2 for the synthesis of certain compounds of general formula 1.
Figure 9:
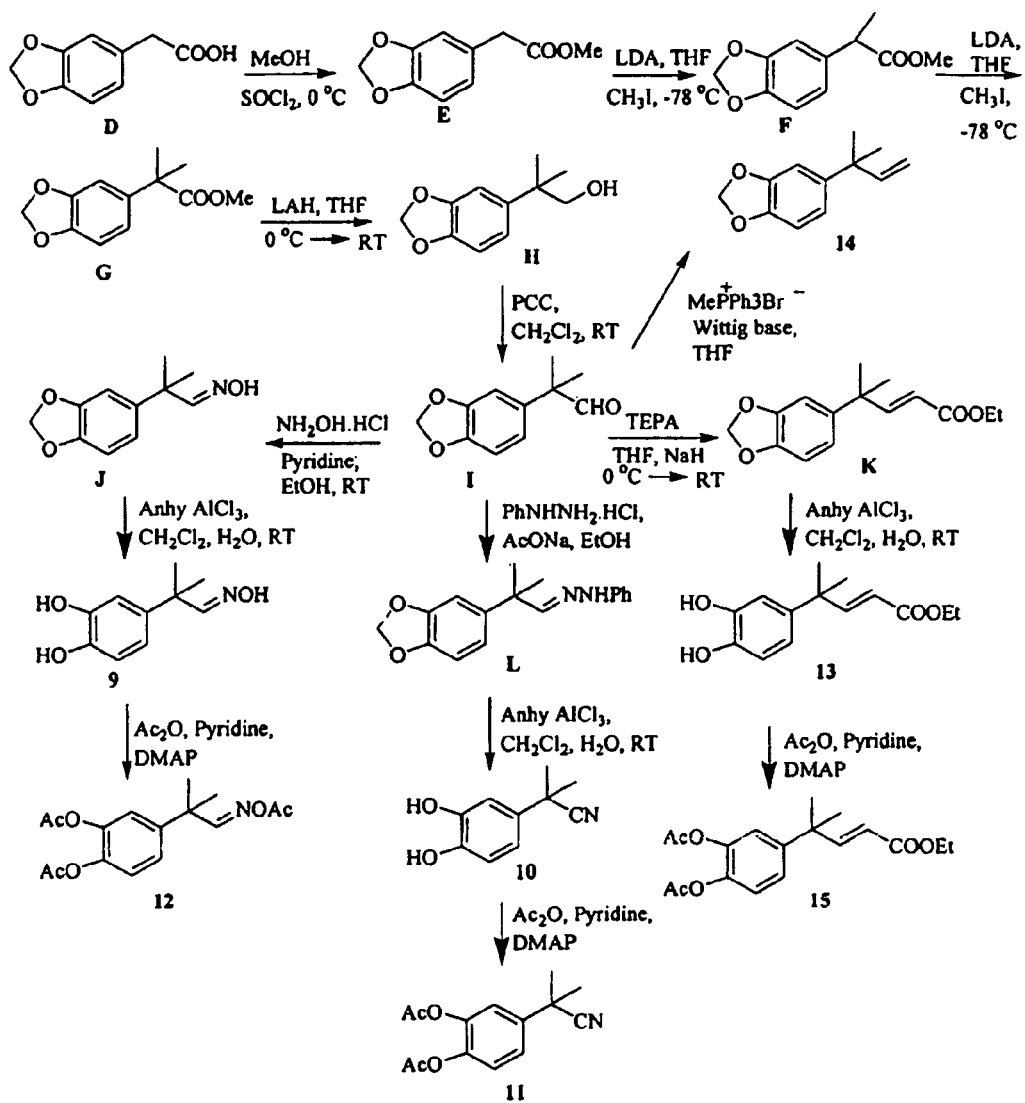
FIG. 9 presents Scheme 3 for the synthesis of certain compounds of general formula 1.

Compound 1 (100 mg/kg body weight) or vehicle control were administered via oral route twice a day for 10 days (5 mice per group). Results are presented in FIG. 6.

Conclusion

The in vivo efficacy of Compound 1 for anticancer activity was further confirmed in human adenocarcionma (MCF-7) xenografts in nude mice.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

The invention has been described with reference to various specific and preferred embodiments and techniques. However, it should be understood that many variations and modifications may be made while remaining within the spirit and scope of the invention.

ADVANTAGES OF THE INVENTION

Present invention provides compounds for the treatment of malignancies (cancer).

Present invention provides compounds for the treatment of malignancies (cancer) of breast, prostate, pancreas, acute lymphoblastic leukemia, and acute/chronic myelogenous leukemia.

Malignancies may be treated by PI3 (phosphatidylinositol-3-kinase) pathway inhibition or by nitric oxide production.

We claim:

1. A compound of general formula 1:

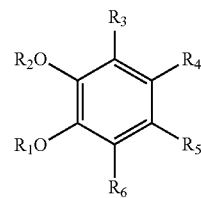

General formula 1 wherein
$R_1$ is one of H or $COCH_3$, and
$R_2$ is H or $COCH_3$,
or $R_1$ and $R_2$ combine to form —$CH_2$—;
$R_3$ is one of H or $CH_2$—CH=$CH_2$, and
$R_4$ is one of H, $CH_2$—CH=$CH_2$, $CH_2$—$CH_2$—$CH_3$, $C(CH_3)_2CH$=NOH,
$C(CH_3)_2CH$=$CH_2$, $C(CH_3)_2CN$, or $C(CH_3)_2CH$=NOCOCH_3,
wherein
in the case that $R_3$ is H, then $R_4$ is $CH_2$—$CH_2$—$CH_3$, $C(CH_3)_2CH=NOH$, $C(CH_3)_2CH=CH_2$, $C(CH_3)_2CN$ or
$C(CH_2)_2CH=NOCOCH_3$, and
in the case that $R_3=CH_2—CH=CH_2$, then $R_4$ is $CH_2—CH=CH_2$, $CH_2—CH_2—CH_3$, $C(CH_3)_2CH=NOH$, $C(CH_3)_2CH=CH_2$, $C(CH_3)_2CN$ or $C(CH_3)_2CH=NOCOCH_3$;

$R_5$ is one of H or $CH_2—CH=CH_2$;
$R_6$ is one of H or $CH_2—CH=CH_2$;
wherein
in the case that $R_4$ is $CH_2—CH_3—CH_3$, then $R_3$ or $R_5$ is $CH_3—CH=CH_2$;
in the case that $R_4$ and $R_3$ combine to form $—CH_2—$, then $R_4$ is $C(CH_3)_2CH=CH_2$; and
in the case that $R_1$ and $R_2$ are each H, then $R_4$ is one of $C(CH_2)_2CH=NOH$, $C(CH_3)_3CN$ or $CH_3—CH_2—CH_3$.

2. A pharmaceutical composition comprising a compound of general formula 1:

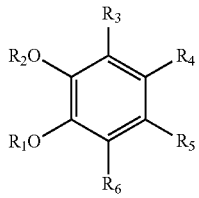

wherein
$R_1$ is one of H or $COCH_3$, and
$R_2$ is one of H or $COCH_3$,
or $R_1$ and $R_2$ to combine to form $—CH_2—$;
$R_3$ is one of H or $CH_2—CH=CH_2$, and
$R_4$ is one of H, $CH_2—CH=CH_2$, $CH_2—CH_2—CH_3$, $C(CH_3)_2CH=NOH$, $C(CH_3)_2CH=CH_2$, $C(CH_3)_2CN$, or $C(CH_3)_2CH=NOCOCH_3$,
wherein in the case that $R_3$ is H, then $R_4$ is $CH_2—CH_2—CH_3$, $C(CH_3)_2CH=NOH$, $C(CH_3)_2CH=CH_2$, $C(CH_3)_2CN$ or $C(CH_3)_2CH=NOCOCH_3$, and
$R_5=H$ or $CH_2—CH=CH_2$;
$R_6=H$ or $CH_2—CH=CH_2$;
wherein
in the case that $R_1$ and $R_2$ combine to form $—CH_3—$, then $R_4$ is $C(CH_3)_2CH=CH_2$; and
in the case that $R_3$ and $R_2$ are each H, then $R_4$ is one of $C(CH_3)_2CH=NOH$, $C(CH_3)_2CN$ or $CH_2—CH_2—CH_3$, wherein the concentration of the compound is 0.1 to 99% by weight in a tablet or capsule; or 3-50% by volume are in a liquid preparation, along with pharmaceutically acceptable additive (s) or excipeint (s).

3. A pharmaceutical composition of claim 2, wherein the compound is selected from the group consisting of:
3,4-diallylbenzene-1,2-diol;
4-allyl-5-propylbenzene-1,2-diol;
4-allyl-5-propyl-1,2-phenylene diacetate;
3-allyl-benzene-1,2-diol; and
3-allyl-1,2-phenylene diacetate.

4. A pharmaceutical composition comprising a compound of claim 1, wherein 0.1 to 99% of the compound by weight is present in a tablet or capsule; or 3-50% by volume is present in a liquid preparation along with pharmaceutically acceptable additive(s) or excipient(s).

5. A pharmaceutical composition of claim 2, wherein the additive(s) or excipient(s) are selected from the group consisting of fillers, antioxidants, dispersants, emulsifiers, flavors, preservatives, solubilizers, and colorants.

6. A pharmaceutical composition of claim 4, wherein the additive(s) or excipient(s) are selected from the group consisting of fillers, antioxidants, dispersants, emulsifiers, flavors, preservatives, solubilizers and colorants.

7. A pharmaceutical composition comprisiong a compound selected from the group consisting of:
(E)-ethyl 4-(3,4-dihydroxyphenyl)-4-methylpent-2-encate; and
(E)-4-(5-ethoxy-2-methyl-5-oxopent-3-en-2-yl)-1,2-phenylene diacetate,
wherein the concentration of the compound is 0.1 to 99% by weight in a tablet or capsule; or 3-50% by volume are in a liquid preparation along with pharmaceutically acceptable additive(s) or excipient(s).

8. A pharmaceutical composition comprising a compound of claim 7, wherein 0.1 to 99% of the compound by weight is present in a tablet or capsule; or 3-50% by volume is present in liquid preparation along with pharmaceutically acceptable additive(s) or excipient(s).

9. A pharmaceutical composition of claim 7,
Wherein the additive(s) or excipient(s) are selected from the group consisting of fillers, antioxidants, dispersants, emulsifiers, flavors, preservatives, solubilizers and colorants.

10. A pharmaceutical composition of claim 8, wherein the additive(s) or excipient(s) are selected from the group consisting of fillers, antioxidants, dispersants, emulsifiers, flavors, preservatives, solubilizers and colorants.

* * * * *